(12) United States Patent  (10) Patent No.: US 6,604,653 B2
Millar  (45) Date of Patent: Aug. 12, 2003

(54) EARPLUG DISPENSER

(75) Inventor: Timothy A. Millar, Carmel, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 0 days.

(21) Appl. No.: 09/891,808

(22) Filed: Jun. 26, 2001

(65) Prior Publication Data

US 2002/0043538 A1 Apr. 18, 2002

Related U.S. Application Data

(60) Provisional application No. 60/214,268, filed on Jun. 26, 2000.

(51) Int. Cl.⁷ .................................................. B65H 3/60
(52) U.S. Cl. ........................................ 221/203; 221/265
(58) Field of Search ................................ 221/203, 248, 221/261, 265, 277, 283, 284

(56) References Cited

U.S. PATENT DOCUMENTS

| | | | |
|---|---|---|---|
| 1,226,218 A | * 5/1917 | Karcher | 221/284 |
| 1,653,286 A | 12/1927 | Huggins | |
| 2,429,510 A | 7/1947 | Callison | |
| 2,494,141 A | * 1/1950 | Perrin et al. | 221/265 |
| 2,543,934 A | * 3/1951 | Poskey | 221/283 |
| 2,923,436 A | * 2/1960 | Koehn | 221/265 |
| 3,730,387 A | * 5/1973 | McConnell et al. | 221/265 |
| 3,804,294 A | 4/1974 | Householder | |
| 3,893,593 A | * 7/1975 | Hazard | 221/265 |
| 4,273,254 A | * 6/1981 | Cuppleditch et al. | 221/196 |
| 5,280,845 A | 1/1994 | Leight | |
| D345,663 S | 4/1994 | Hartman et al. | |
| 5,322,185 A | * 6/1994 | Leight | 221/203 |
| 5,954,229 A | 9/1999 | Scholey et al. | |
| 6,241,120 B1 | 6/2001 | Scholey et al. | |
| 6,299,019 B1 | * 10/2001 | Leight | 221/265 |

FOREIGN PATENT DOCUMENTS

| | | | | |
|---|---|---|---|---|
| EP | 1 074 236 | | 2/2001 | |
| WO | WO 94/09456 | * | 4/1994 | 221/203 |

* cited by examiner

*Primary Examiner*—Kenneth W. Noland
(74) *Attorney, Agent, or Firm*—Cantor Colburn LLP

(57) ABSTRACT

A mechanism for dispensing earplugs is provided, including a container for storing the earplugs, the container having at least one container opening through which the earplugs are dispensed, a shutter assembly located at the container opening, the shutter assembly having at least one shutter opening formed therein, and a funnel member attached to the shutter assembly for guiding dispensed earplugs to an operator. The shutter assembly of the present invention moves to bring the shutter opening into alignment with the container opening thus allowing the earplugs to pass from the earplug container, through the shutter assembly, into the dispensing flange, and to the operator.

18 Claims, 25 Drawing Sheets

EARPLUG DISPENSER

CROSS-REFERENCE TO RELATED APPLICATIONS

This application claims the benefit of the filing date of U.S. Provisional Application Ser. No. 60/214,268, filed Jun. 26, 2000, which is incorporated herein in its entirety.

FIELD OF THE INVENTION

The present invention relates generally to ear protection, and more particularly to a manually operated earplug dispenser.

DESCRIPTION OF RELATED ART

Disposable earplugs are used in large quantities in manufacturing and industrial operations. Convenient access to earplugs on-site is essential to ensure worker safety and to enhance operating efficiency.

Traditional methods of earplug distribution include providing a large open box of individual earplugs for workers to access as needed. Often, however, workers will inadvertently acquire more earplugs than are necessary when accessing the box by hand. Extra earplugs are commonly discarded about the work space, wasting the earplugs and requiring subsequent clean-up efforts. Additionally, sanitization of the earplugs is jeopardized in such a free-for-all distribution.

In another traditional method of earplug distribution, earplugs are packaged in pairs and placed in large open boxes proximate to manufacturing and industrial sites. Workers may then access the packaged plugs by hand ensuring only two plugs are attained at any one time and preserving the sanitization of the wrapped earplugs. This system of earplug distribution, however, substantially increases the cost of manufacturing the earplugs as now a packaging step is required. Further, wrapped earplugs result in unnecessary waste as the packaging is used only once and then discarded, often on the floor of the workspace, thus requiring subsequent clean up.

Recent advances in earplug distribution methods include utilizing stand alone or wall-mount dispensing mechanisms. FIGS. 1 and 2 show various views of a traditional earplug dispenser 10. The dispenser 10 generally includes a mount assembly 12 to which an earplug container 14 is affixed. A rotatable impeller assembly 16 is located within the earplug container 14 for facilitating dispensing of earplugs 18 which are stored within the earplug container 14. The impeller assembly 16 includes a wheel 20 having impeller openings 22 formed therein. The impeller assembly 16 also includes a raised portion 24 formed centrally on the wheel 20 to promote movement of the earplugs 18 within the container 14 toward the impeller openings 22. Further, the impeller assembly 16 includes a knob portion 26 which extends generally from the raised portion 24 to the exterior of the earplug container 14.

The impeller assembly 16 is traditionally a uniform construction of integrally molded plastics and is designed to manually rotate within the earplug container 16. An operator of the traditional earplug dispenser 10 rotates, by hand, the knob portion 26 thus turning the wheel 20 within the earplug container 14. The impeller openings 22 are intended to catch individual earplugs 18 and traverse them about a base 28 of the earplug container 14 toward a dispensing opening 30 through which the earplugs 18 pass into a hand of the operator.

However, due to the pliable nature of compositions commonly used to manufacture earplugs, rotation of the wheel 20 is often inhibited by the earplugs 18 becoming jammed between edges of the impeller openings 22 and the base 28 of the earplug container 14 as the earplugs 18 are dragged towards the dispensing opening 30. Inhibited rotation of the wheel 20 greatly reduces the overall efficiency of the earplug dispenser 10. Further, such jammed earplugs 18 are compressed under the forces exerted by the rotating wheel 20, thus, decreasing in size and allowing additional earplugs 18 to enter the particular impeller opening 22. This often results in several earplugs 18 being passed through the dispensing opening 30 at a time. The operator of the dispenser 10 generally needs only two earplugs, the excess of which are typically discarded resulting in waste and degrading the efficiency of the earplug dispenser 10.

Further, the traditional earplug dispenser 10 is suitable for allowing the passage of only certain earplugs 18. That is, conventionally, the impeller openings 22 and the dispensing opening 30 are designed so as to provide the passage therethrough of specified earplugs 18 of a particular size and shape. Additionally, the traditional dispenser 10 functions properly only in conjunction with earplugs 18 of a designated material composition. Therefore, the earplug dispenser 10 typically may not be used with earplugs of varying shapes, sizes, and materials, thus reducing the flexibility and overall efficiency of the traditional earplug dispenser 10.

Thus, an earplug dispenser is desired which ensures sanitation of earplugs plugs contained therein while allowing efficient, effective, and consistent distribution of earplugs of a variety of shapes, sizes, and compositions.

SUMMARY OF THE INVENTION

According to the present invention, a mechanism for dispensing earplugs is provided. The mechanism generally includes a container for storing the earplugs, a dispensing assembly attached to the container for dispensing the earplugs, and a mounting assembly for releasably retaining the earplug container and the dispensing assembly.

The mounting assembly of the present invention includes a base for supporting the mechanism. A neck is mounted to the base and rises vertically therefrom. The mounting assembly also includes an upper portion mounted to the neck. The upper portion receives and retains the earplug container and the dispensing assembly. The mounting assembly may stand freely upon the base supporting the earplug container and the dispensing assembly thereupon or the mounting assembly may alternatively be mounted to a vertical support by fastening the neck thereto.

The earplug container of the present invention is substantially a storage bin for containing the earplugs and includes an opening through which the earplugs may pass. The earplug container is shaped so as to promote the movement of earplugs toward the opening.

The dispensing assembly is mounted to the earplug container at the container opening. The dispensing assembly allows a selective dispensation of the earplugs from the container.

The dispensing assembly includes a channel plate releasably mounted to the container at the opening. The channel plate includes a plurality of channels formed therein through which the earplugs are dispensed. The channel plate also includes a through opening formed centrally therein.

The dispensing assembly further includes a shutter plate located adjacent the channel plate, opposite the earplug container. The shutter plate includes a shutter opening formed therein.

The dispensing assembly also includes an impeller located within the earplug container adjacent the channel plate. The impeller is attached to the shutter plate through the through hole of the channel plate. In this way, the shutter plate and the impeller may rotate relative to the channel plate selectively bringing the shutter opening into alignment with the channels of the channel plate, thus allow passage of the earplugs therethrough.

Further, the dispensing assembly includes a funnel fixably attached to the shutter plate such that rotation of the funnel correspondingly rotates the shutter plate and the impeller.

An operator of the earplug dispensing mechanism of the present invention rotates, by hand, the funnel of the dispensing mechanism. Such rotation correspondingly rotates the shutter plate and the impeller. The rotation of the impeller within the earplug container stirs the earplugs and settles the earplugs toward the channel plate, prompting the earplugs to enter the channels. Rotation of the shutter plate beneath the channel plate circumferentially moves the shutter opening relative to the channel plate. The shutter opening selectively aligns with the channels thus allowing an earplug located within the respective channel to pass through the shutter opening and into the funnel. The funnel guides the dispensed earplug to the awaiting hand of the operator.

The earplug dispensing mechanism of the present invention allows discrete dispensation of earplugs while maintaining the integrity of the earplugs within the container therefore not requiring the earplugs be packaged in any way, thus eliminating the waste typically associated with the use of packaged earplugs. Further, the earplug dispensing mechanism, as taught herein, prevents against dispensing earplugs in amounts in excess of that required by a particular operator, thus further reducing overall waste and increasing dispensation efficiency. Additionally, the mechanism provided does not cause dragging of the earplugs about the base of the earplug container toward a dispensing opening. In this way, the present invention avoids the frictional forces associated with dragging, thus preventing jamming of the mechanism, hence increasing overall efficiency and usability. Further, due to the novel design of the channels formed within the channel plate, the dispensing assembly of the present invention may accommodate and allow passage therethrough of earplugs of a variety of shapes, sizes, and material compositions.

The above-discussed and other features and advantages of the present invention will be appreciated and understood by those skilled in the art from the following detailed description and drawings.

BRIEF DESCRIPTION OF THE DRAWINGS

To Referring to the FIGURES wherein like elements are numbered alike in the several FIGURES.

Iris

DESCRIPTION OF THE PREFERRED EMBODIMENT

Figure 1:
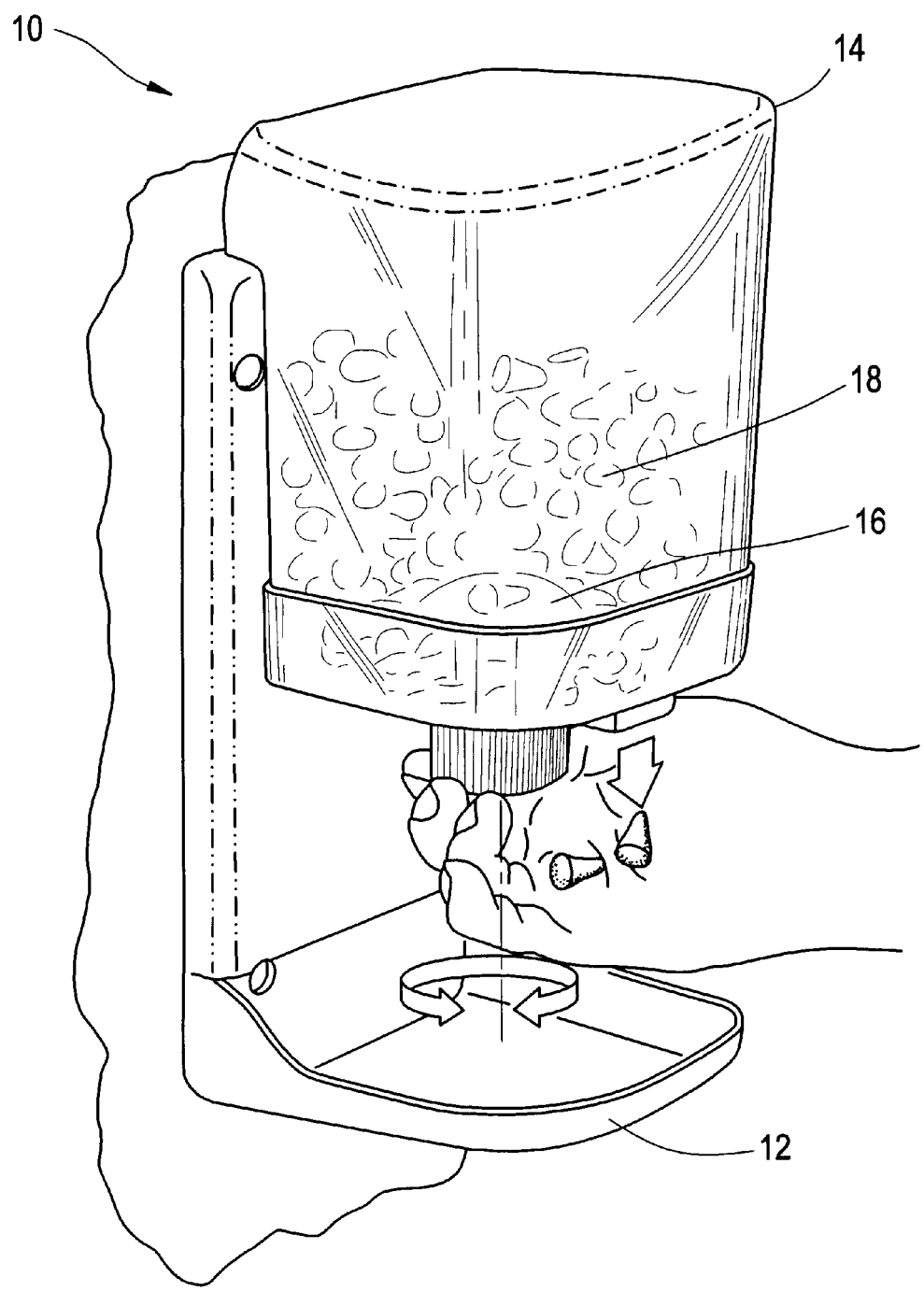
FIG. 1 is a perspective view of a traditional earplug dispenser.
Figure 2:
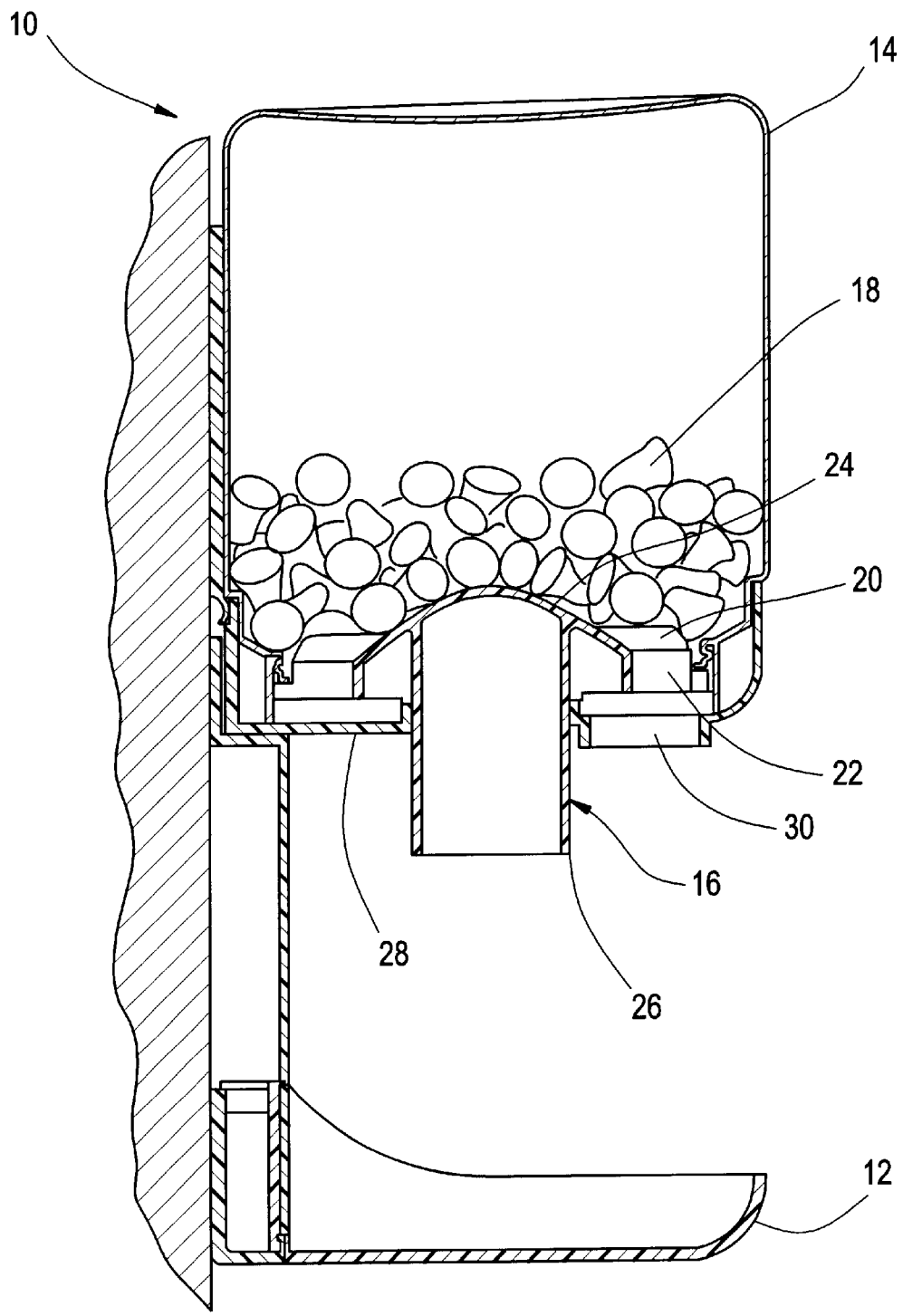
FIG. 2 is a cross-sectional view of the traditional earplug dispenser of FIG. 1.
Figure 3A:
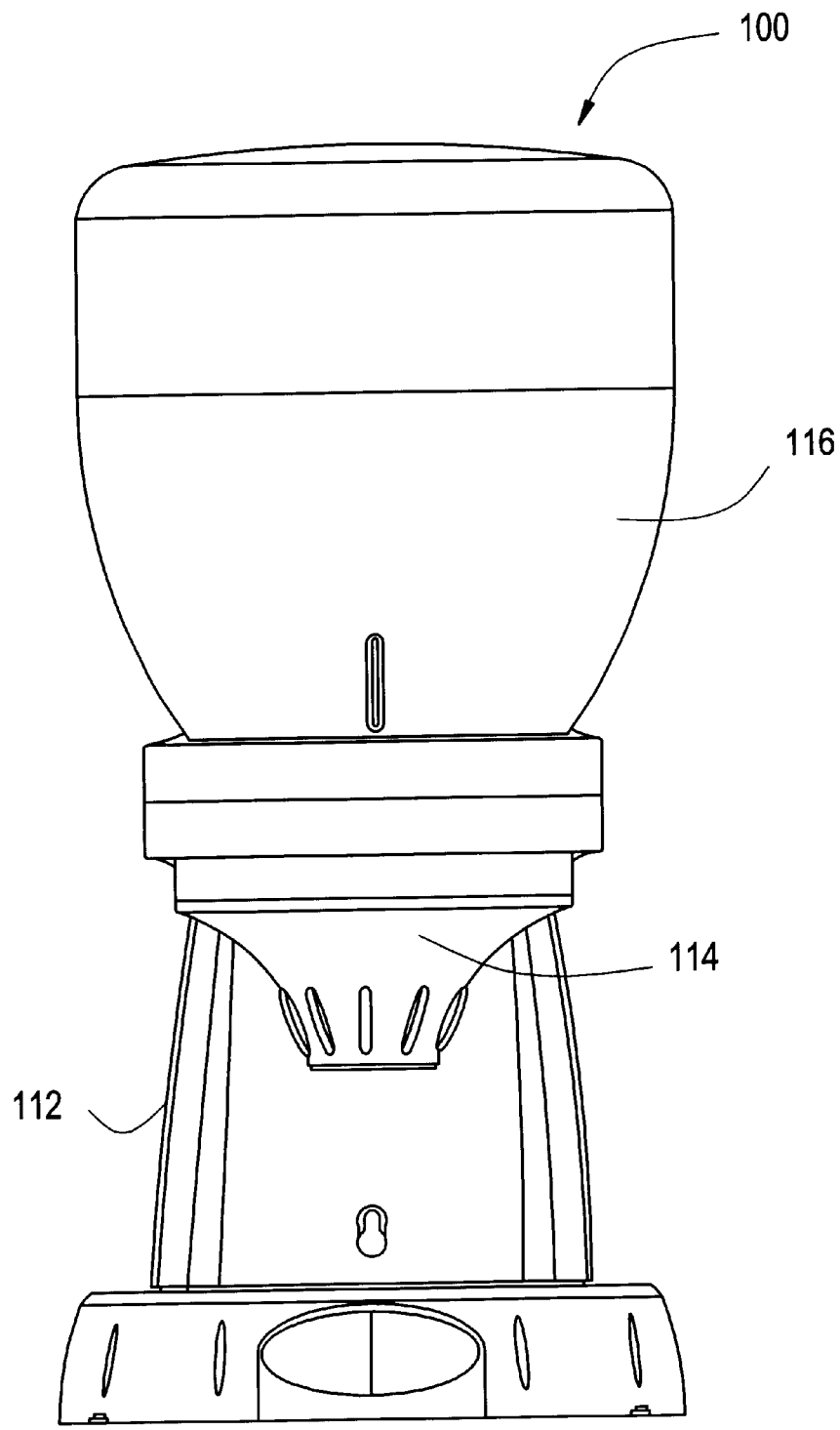
FIGS. 3A and 3B are front elevational views of an earplug dispenser according to one embodiment of the present invention.
Figure 3B:
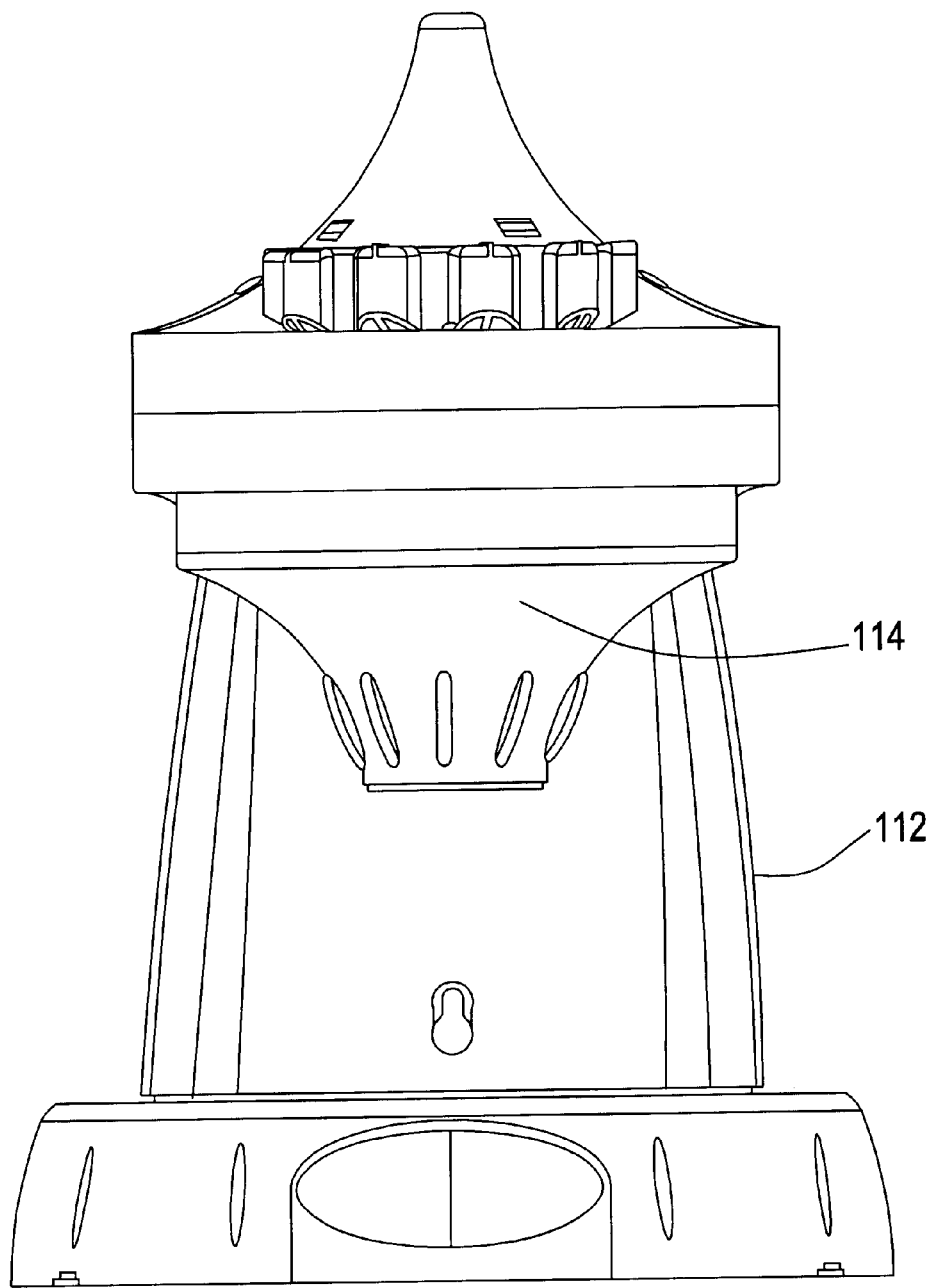
Figure 4:
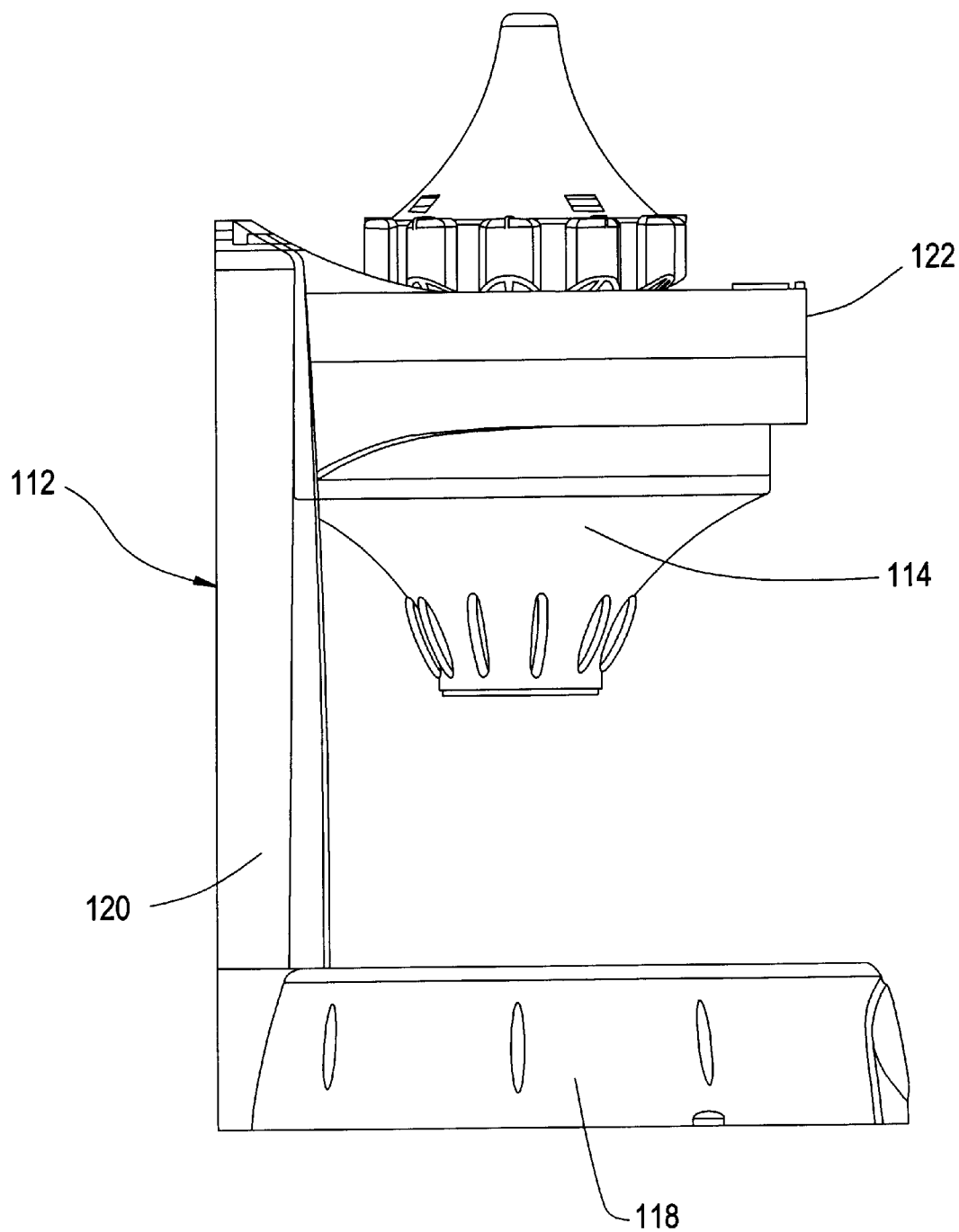
FIG. 4 is a side elevational view of a mounting assembly having a dispensing assembly disposed therein according to one embodiment of the present invention.

FIGS. 3A–3B show an earplug dispenser 100 according to one embodiment of the present invention. The dispenser 100 generally includes a mounting assembly 112 to which a dispensing assembly 114 and an earplug container 116 are affixed. As will be described in greater detail hereinafter, the earplug dispenser 100 is designed to selectively dispense earplugs (not shown) to a user.

Figure 8:
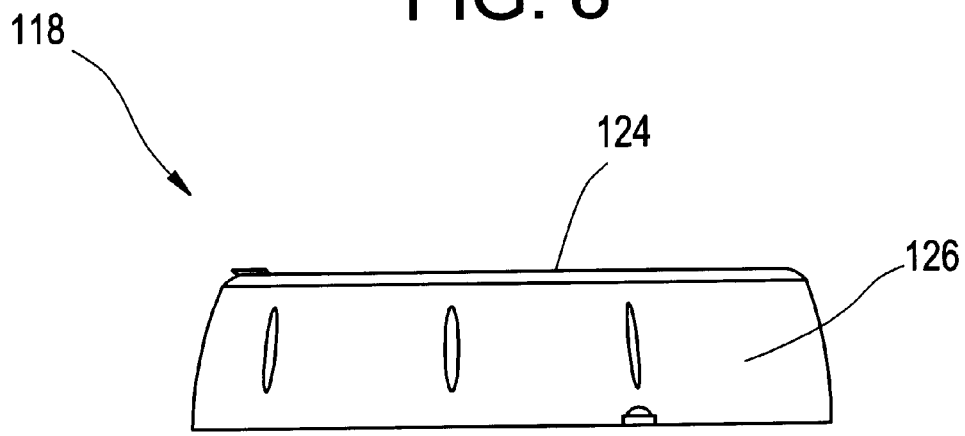
FIG. 8 is a side elevational view of a base of the mounting assembly according to one embodiment of the present invention.
Figure 9:
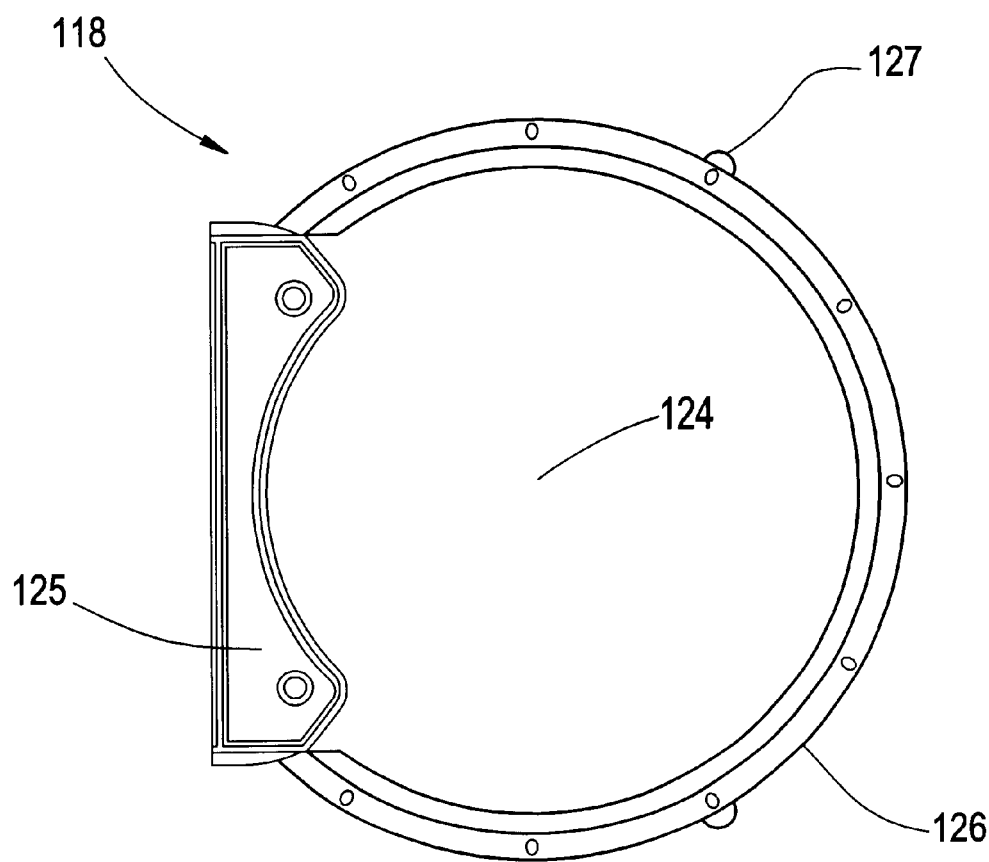
FIG. 9 is a top plan view of the base of FIG. 8.
Figure 10:
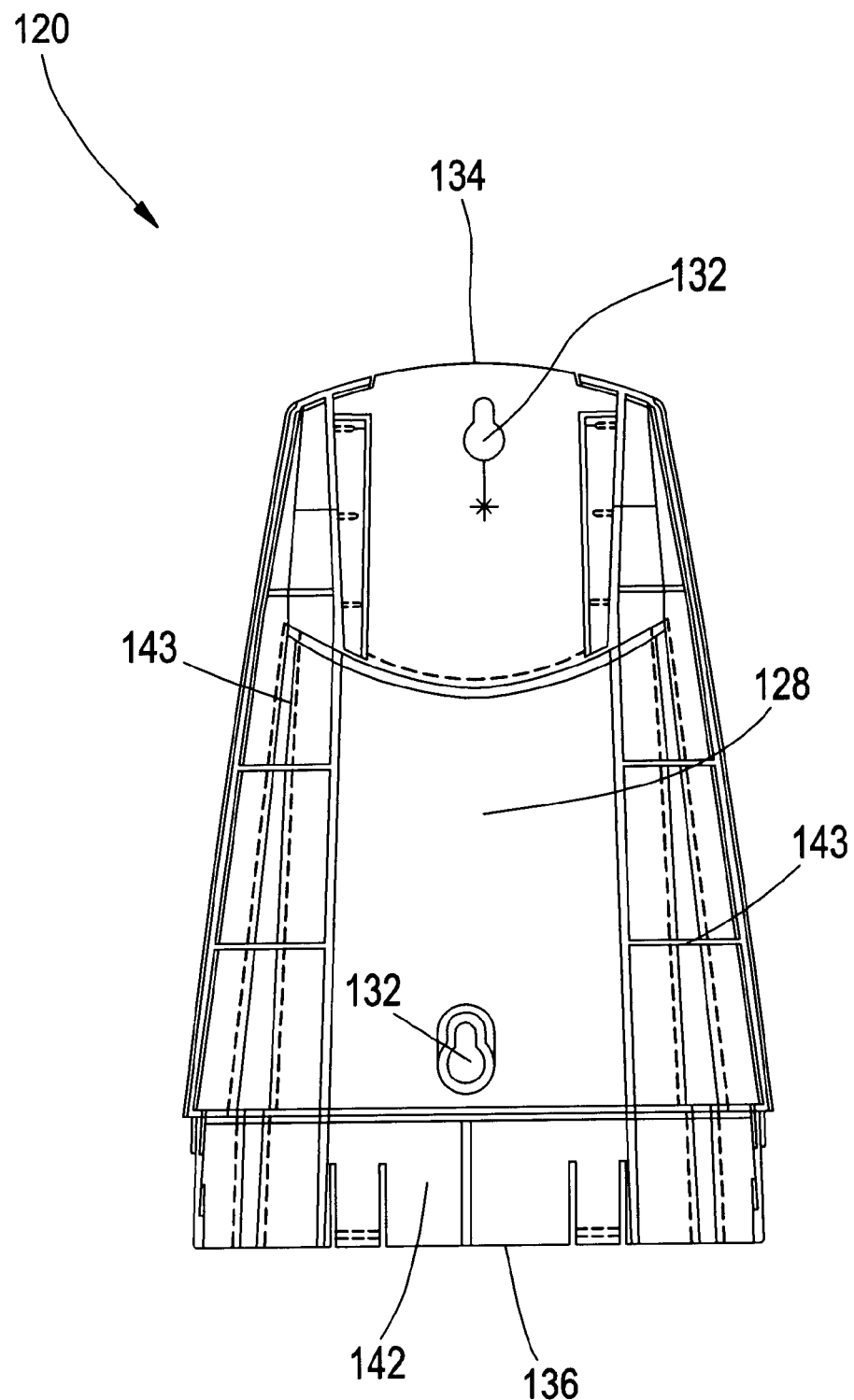
FIG. 10 is a rear view of a neck of the mounting assembly according to one embodiment of the present invention.
Figure 11:
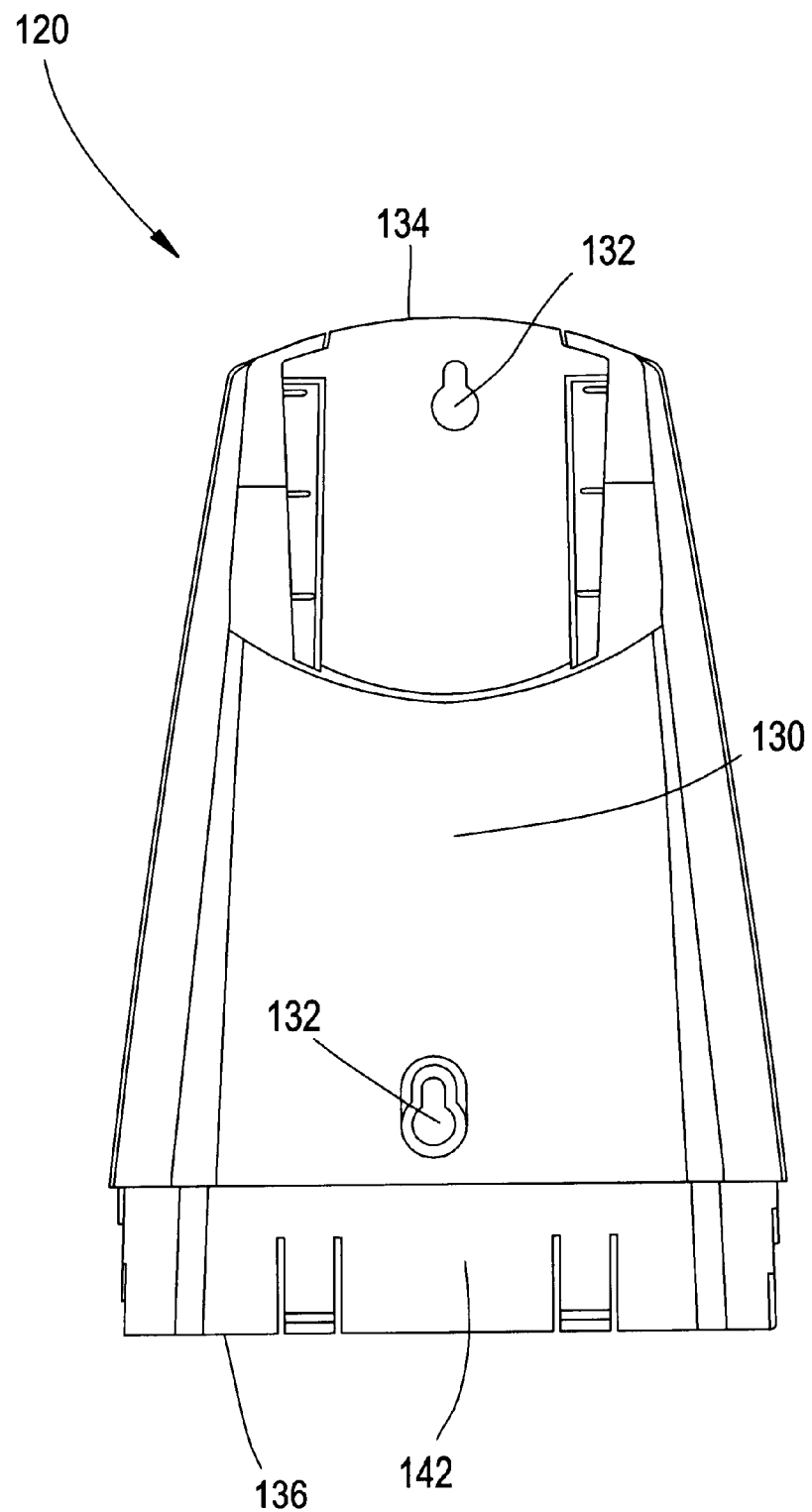
FIG. 11 is a front elevational view of the neck of FIG. 10.
Figure 12:
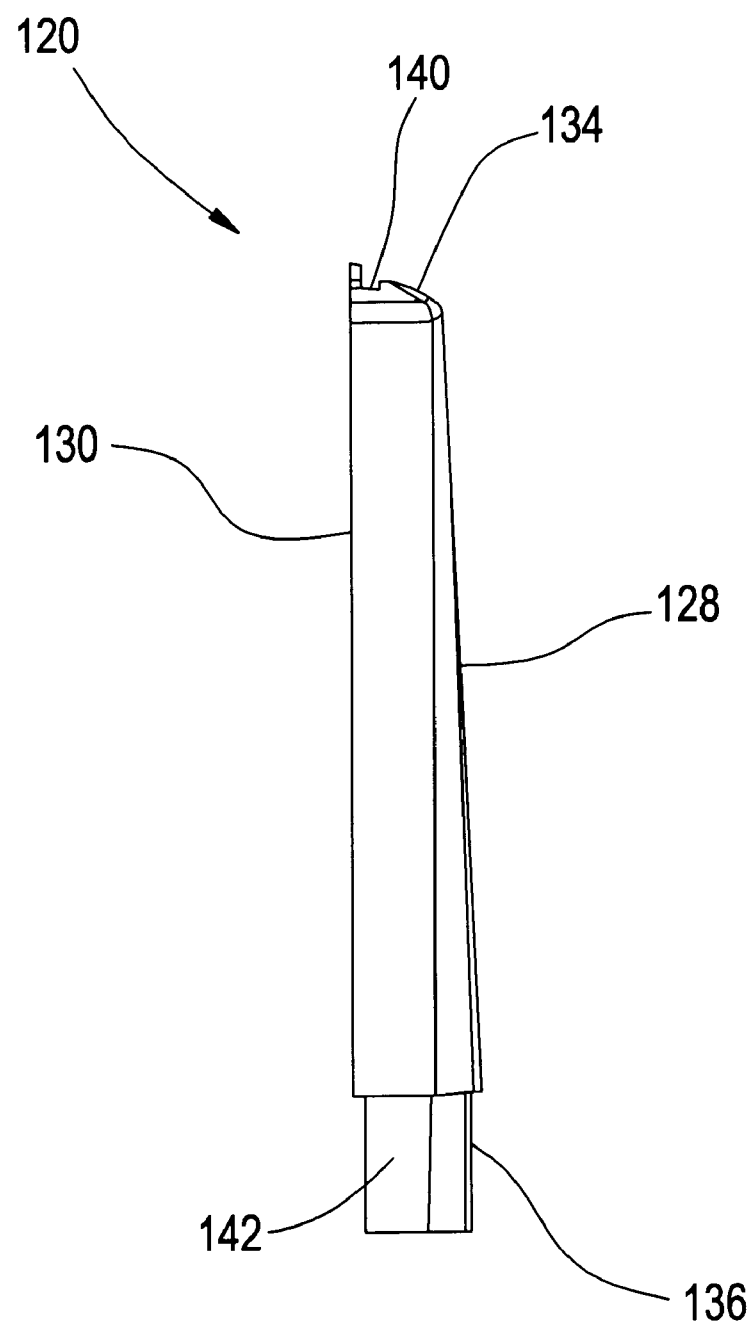
FIG. 12 is a side elevational view of the neck of FIG. 10.

Referring to FIGS. 4–9, the mounting assembly 112 includes a base 118 which receives and releasably retains a neck member 120. Likewise, the neck member 120 receives and releasably retains an upper portion 122 to form the mounting assembly 112. FIGS. 8–9 show various views of the base 118 as being substantially disk-shaped and having an annular top surface 124 and a side peripheral edge 126. The side edge 126 may be formed perpendicular to the top surface 124 or pitched outward to provide the mounting assembly 112 with greater stability, as discussed herein. The base 118 further includes a bracket 125 located at the side edge 126. The bracket 125 receives and releasably retains the neck member 120. The base 118 may further include footings 127 formed on the side edge 126 distal the top surface 124 to provide stability to the base 118 so that the dispenser 100 may be conveniently displayed and positioned on a planar surface.

The neck member 120, as shown in FIGS. 10–13, is a thin, elongated member having a front side 128. The neck member 120 correspondingly has a rear side 130 formed opposite the front side 128. Further, the neck member 120 includes a top side 134 and a bottom side 136 formed opposite one another on the neck member 120. Mounting holes 132 are formed in the neck member 120 and allow passage from the front side 128 to the rear side 130. In one embodiment, fasteners (not shown) are inserted from the front side 128 through the mounting holes 132 to the rear side 130 where the fasteners are secured to a wall, for example, thus affixing the neck member 120 and, hence, as will be shown, the mounting assembly 112 to the wall. The mounting holes 132 may include two holes, one formed proximate the top side 134, the other formed proximate the bottom side 136. The front side 128 includes a slide latch 138 formed proximate the top side 134. The top side 134 also includes a notch 140 located proximate the slide latch 138. The neck member 120 further includes a mounting feature 142 formed proximate the bottom side 136. The mounting feature 142 is received by the bracket 125 thus releasably mounting the neck member 120 to the base 118 (see FIG. 9). Finally, the neck member 120 may include inner flanges 143 located within the neck member 120 to provide support and stability.

Figure 13:
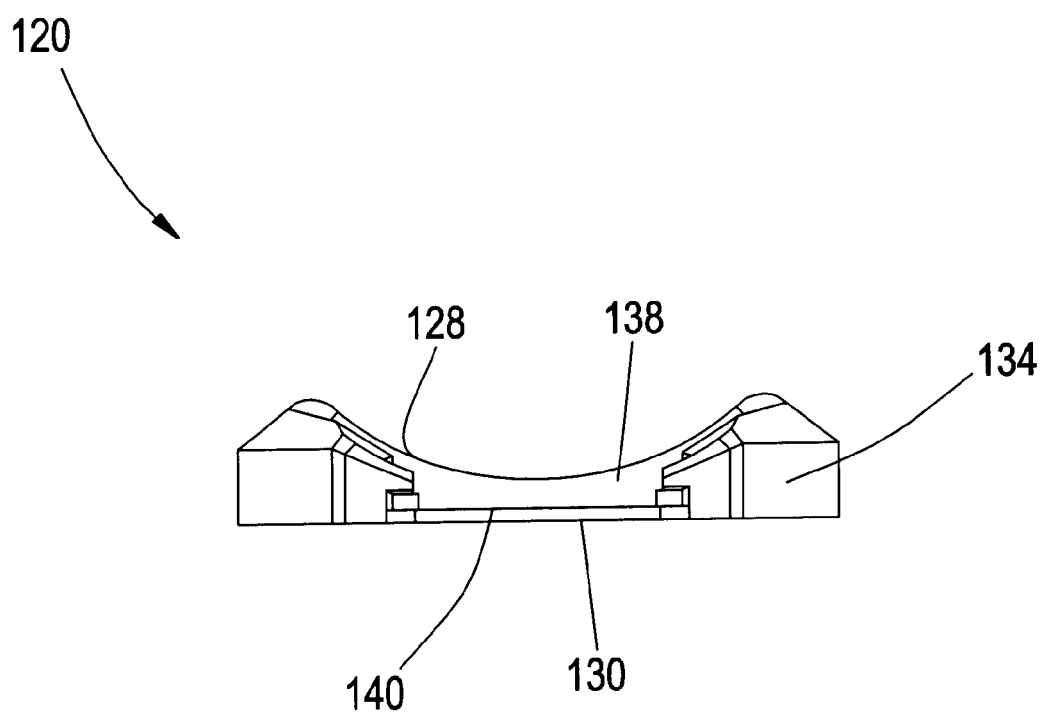
FIG. 13 is a top plan view of the neck of FIG. 10.
Figure 14:
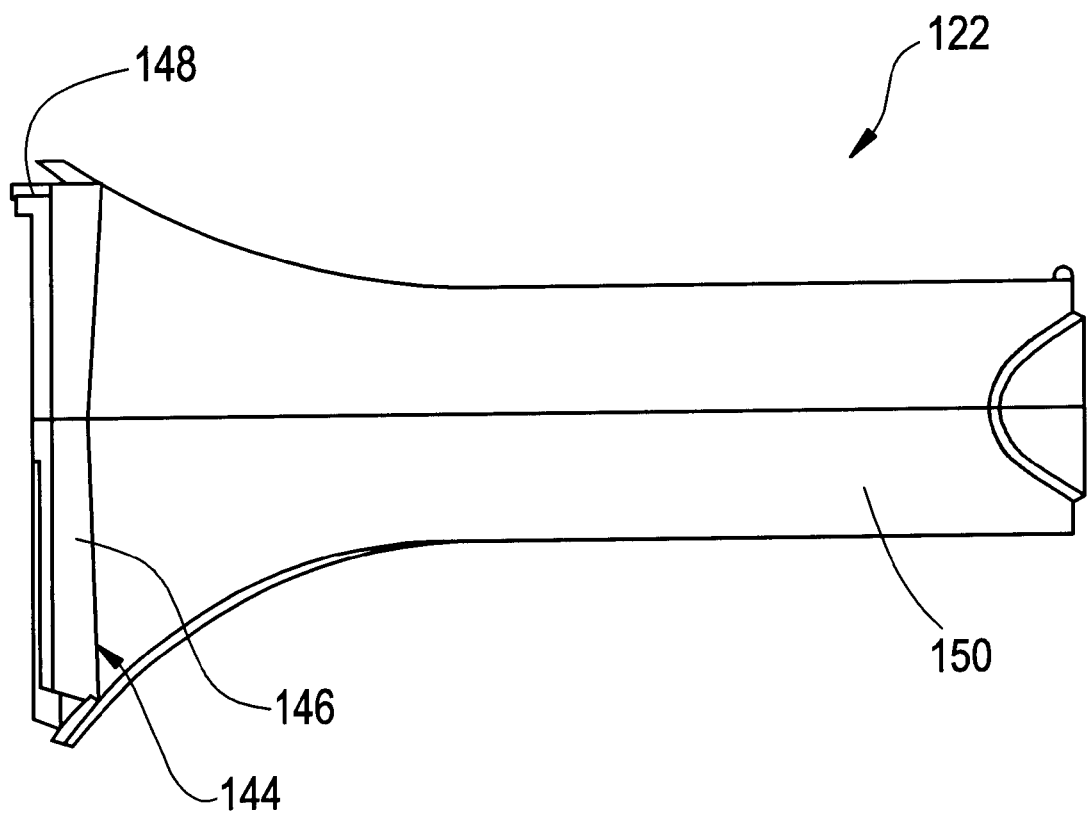
FIG. 14 is a side elevational view of a top portion of the mounting assembly according to one embodiment of the present invention.
Figure 15:
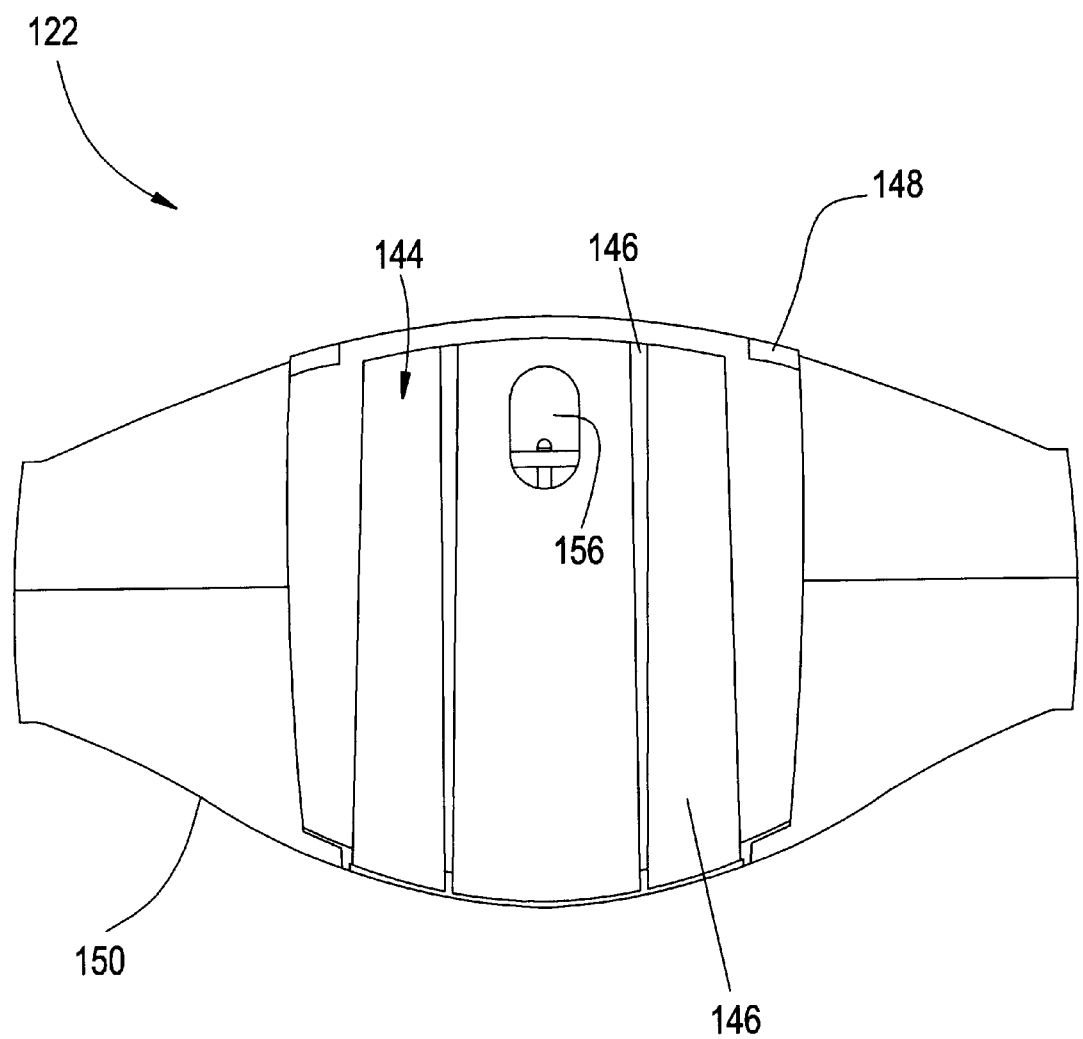
FIG. 15 is a rear elevational view of the top portion of FIG. 14.
Figure 16:
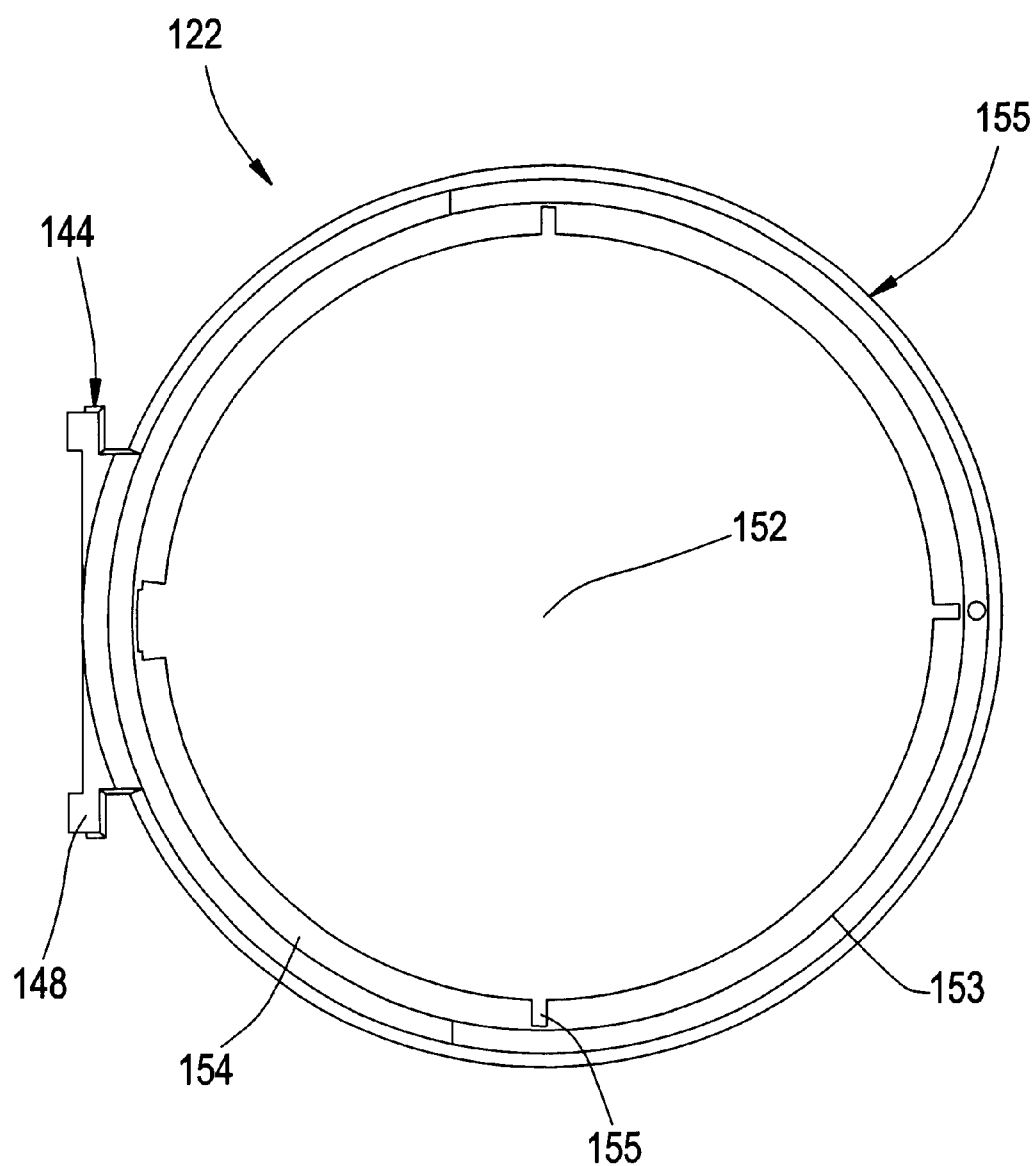
FIG. 16 is a top plan view of the top portion of FIG. 14.

The upper portion 122 of the mounting assembly 112, as shown in FIGS. 14–16, includes a bracket 144 having a key feature 146 which mates with the slide latch 138 to secure the upper portion 122 to the neck 120 (see FIG. 13). The bracket 144 further includes a notch flange 148 for mating with the notch 140 to further secure the upper portion 122 and the neck 120 (see FIG. 12). Additionally, the upper portion 122 includes a ring mount 150 formed integrally with the bracket 144 and extending substantially perpendicular. The ring mount 150 is substantially annular in shape and may be constructed of, for example, a thin plastic material. The ring mount 150 includes a mounting lip 154 located within the ring mount 150, the mounting lip 154 being substantially annular in description concentric with the shape of the ring mount 150. Notches formed in the mounting lip 154 form assembly mounts 155 of varying sizes. The ring mount 150 further includes an opening 152 formed therein defined by the mounting lip 154. The ring mount 150 further includes an inner edge 153. The upper portion 122 further includes a mounting hole 156 formed at the interface of the bracket 144 and the ring mount 150. The mounting hole 156 provides a passage from the opening 152, through the ring mount 150, and through the bracket 144. The mounting hole 156 is located to align with the mounting hole 132 of the neck 120 shown in FIG. 10, thus a fastener (not shown) may be used to secure the upper portion 122 to the neck 120 and, further, as desired, the fastener may be secured to the wall for example, thus affixing the upper portion 122 and the neck 120 thereto. The upper portion 122 of the mounting assembly 112 receives and releasably retains the dispensing assembly 114 of FIGS. 3A–B within the opening 152 as described herein.

Now, with reference to FIGS. 8–16, the assemblage of the mounting assembly 112 is discussed. The bracket 125 of the base 118 receives the mounting feature 142 located on the bottom side 136 of the neck member 120. The mounting feature 142 may mate with the base 118 in a latching manner as to ensure the attachment thereto. Next, the upper portion 122 is attached to the front side 128 of the neck member 120. The slide latch 138 formed on the top side 134 of the neck member 120 receives the bracket 144 of the upper portion 122. The key feature 146 of the bracket 144 slidably engages the slide latch 138 and the notch flange 148 of the bracket 144 mates with the notch 140 to secure the upper portion 122 to the neck 120, thus forming the mounting assembly 112 of FIGS. 3A–3B.

Figure 17:
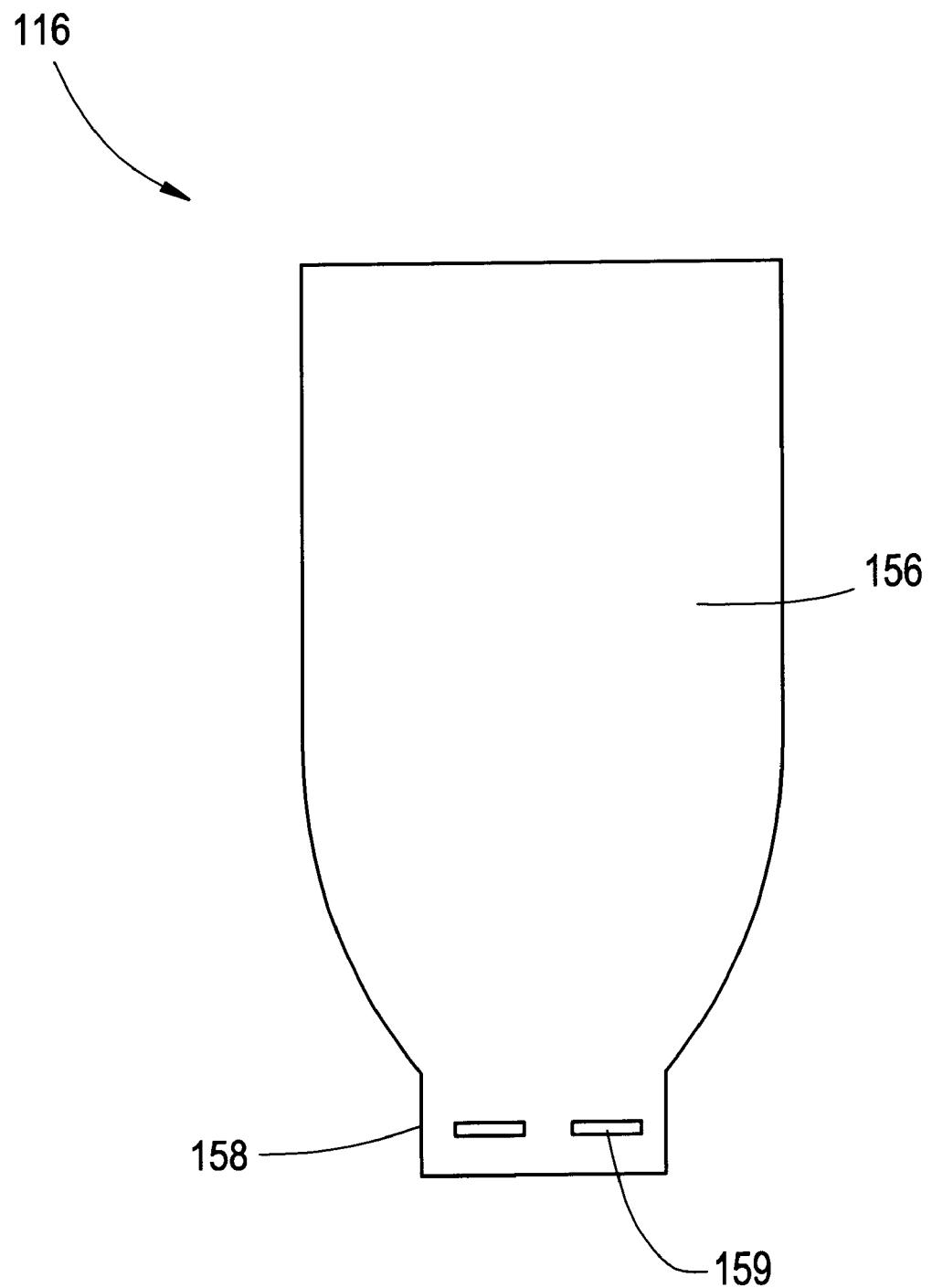
FIG. 17 is a side elevational view of one exemplary earplug container of the present invention.

With reference to FIG. 17, the earplug container 116 includes a hopper portion 156 and a mouth portion 158 formed integrally relative to one another. The hopper portion 156 serves as a storage bin area for the earplugs (not shown) within the earplug dispenser 100. The hopper portion 156 may be cylindrical or funnel shaped with a hollow interior, the hopper portion 156 being designed to promote movement of the earplugs toward the mouth portion 158. The mouth portion 158 defines an opening (not shown) formed therein to allow passage of the earplugs from the hopper portion 156 to the exterior of the earplug container 116. The mouth portion 158 is preferably located beneath the hopper portion 156, thus allowing gravity to draw the earplugs toward the opening. The mouth portion 158 further includes mounting flanges 159 formed thereon to facilitate mating the earplug container 116 with the dispensing assembly 114, as taught below. The container 116 may be made of a translucent or transparent material, for example plastic, to allow visual monitoring of the volume of stored earplugs during usage of the dispenser 100.

Figure 5:
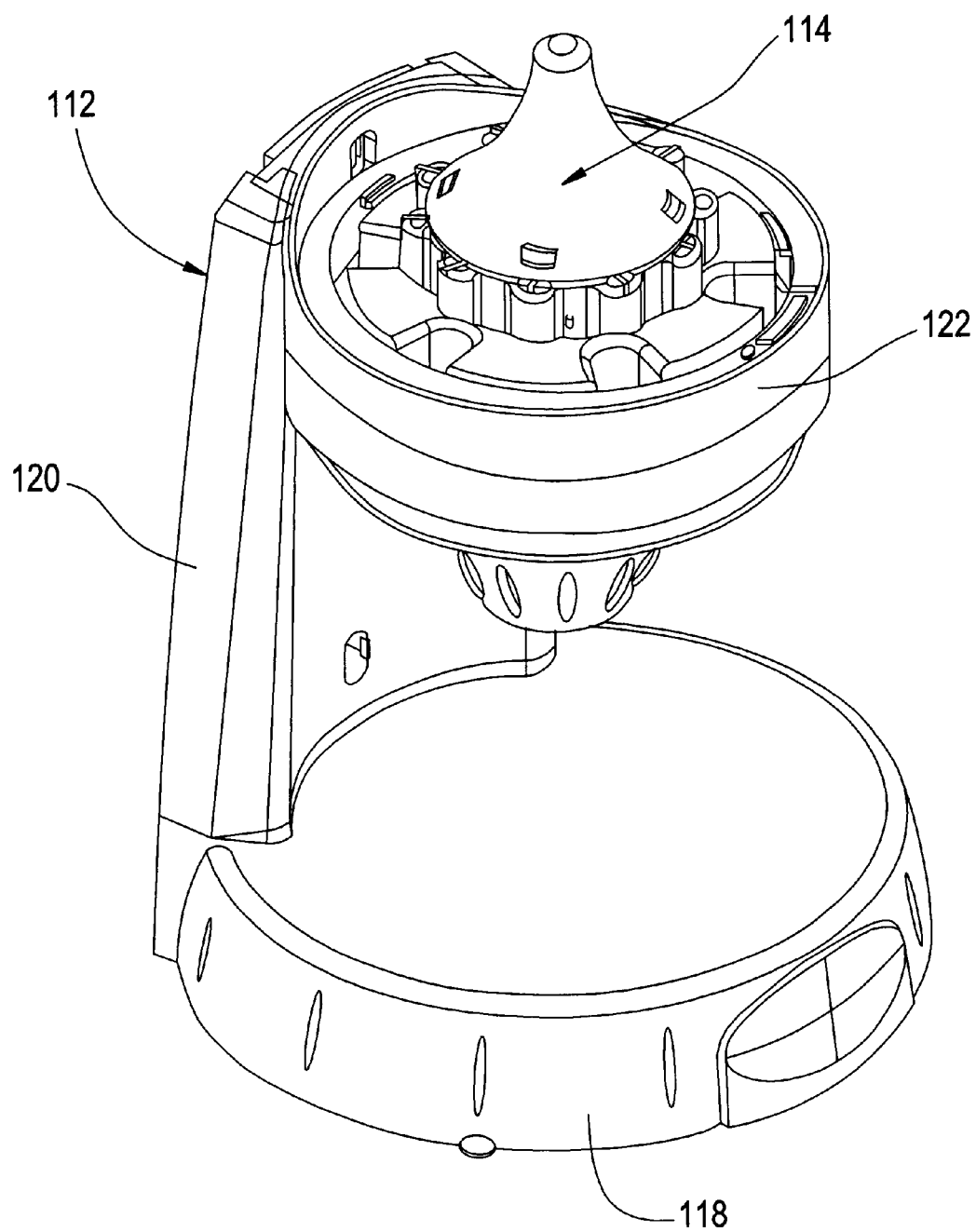
FIG. 5 is a perspective view of the mounting assembly with dispensing assembly of FIG. 4.
Figure 6:
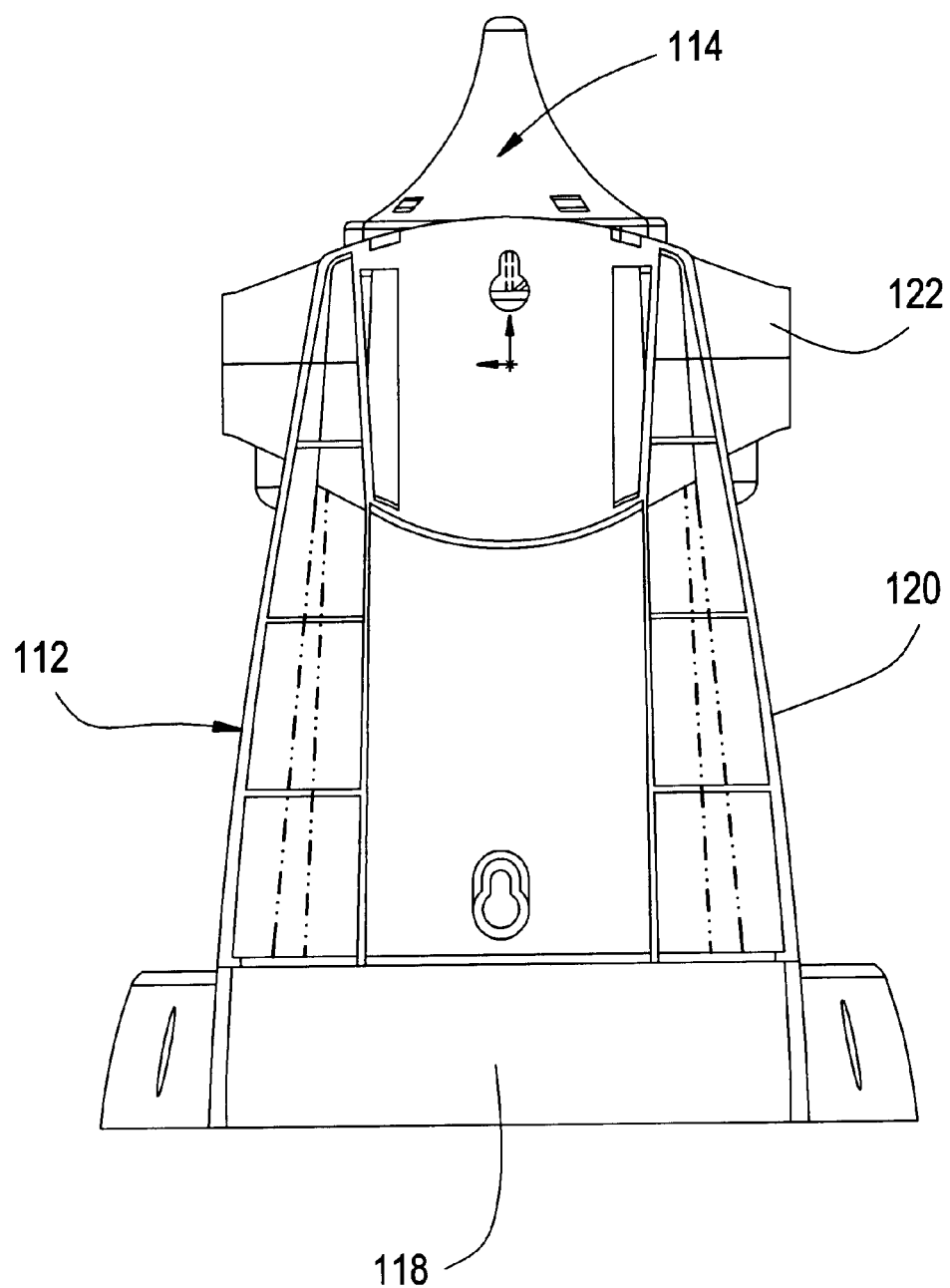
FIG. 6 is a rear elevational view of the mounting assembly with dispensing assembly of FIG. 4.
Figure 7:
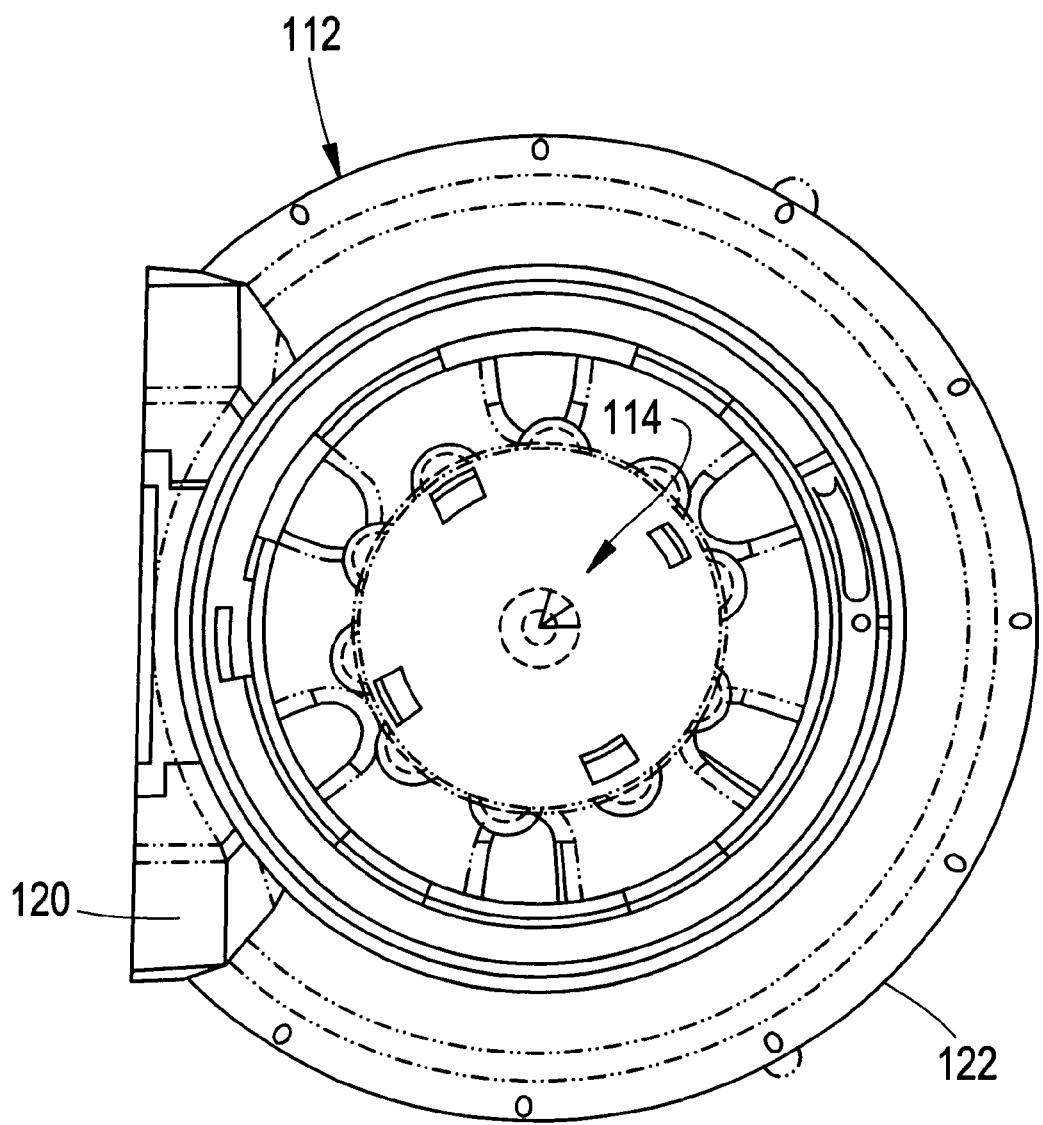
FIG. 7 is a top plan view of the mounting assembly with dispensing assembly of FIG. 4.
Figure 18:
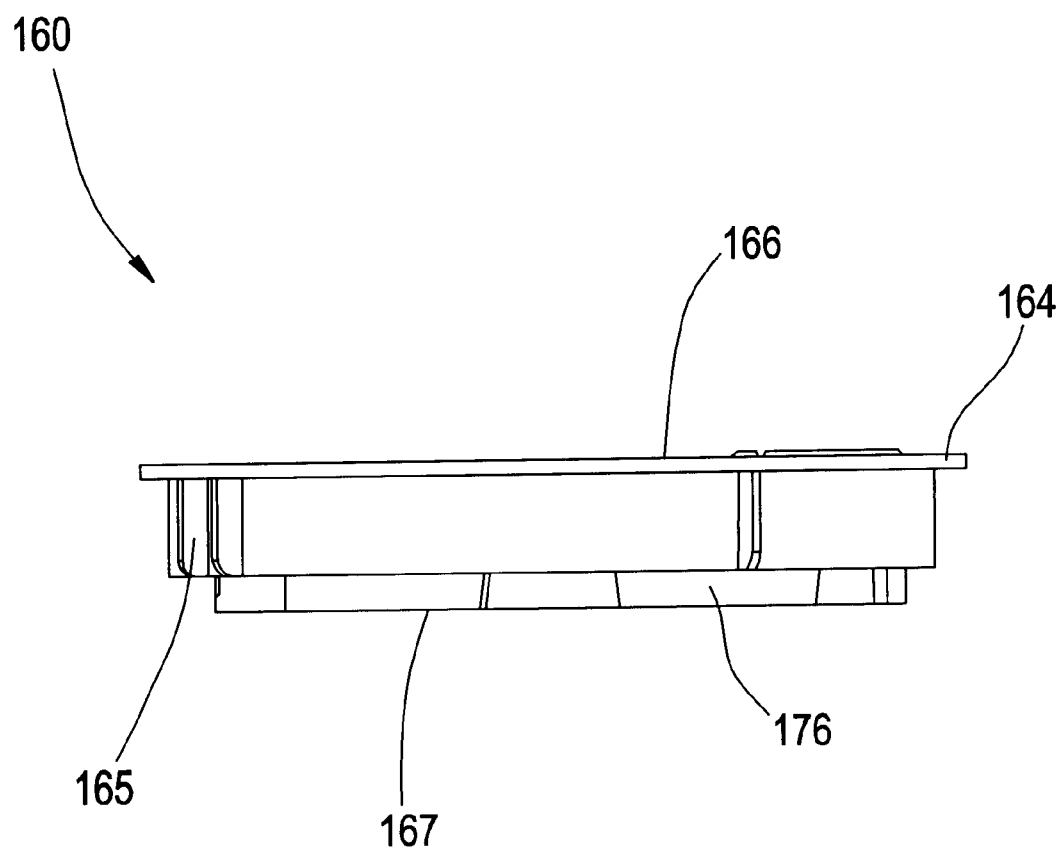
FIG. 18 is a side elevational view of a channel plate in one embodiment according to the present invention.
Figure 19:
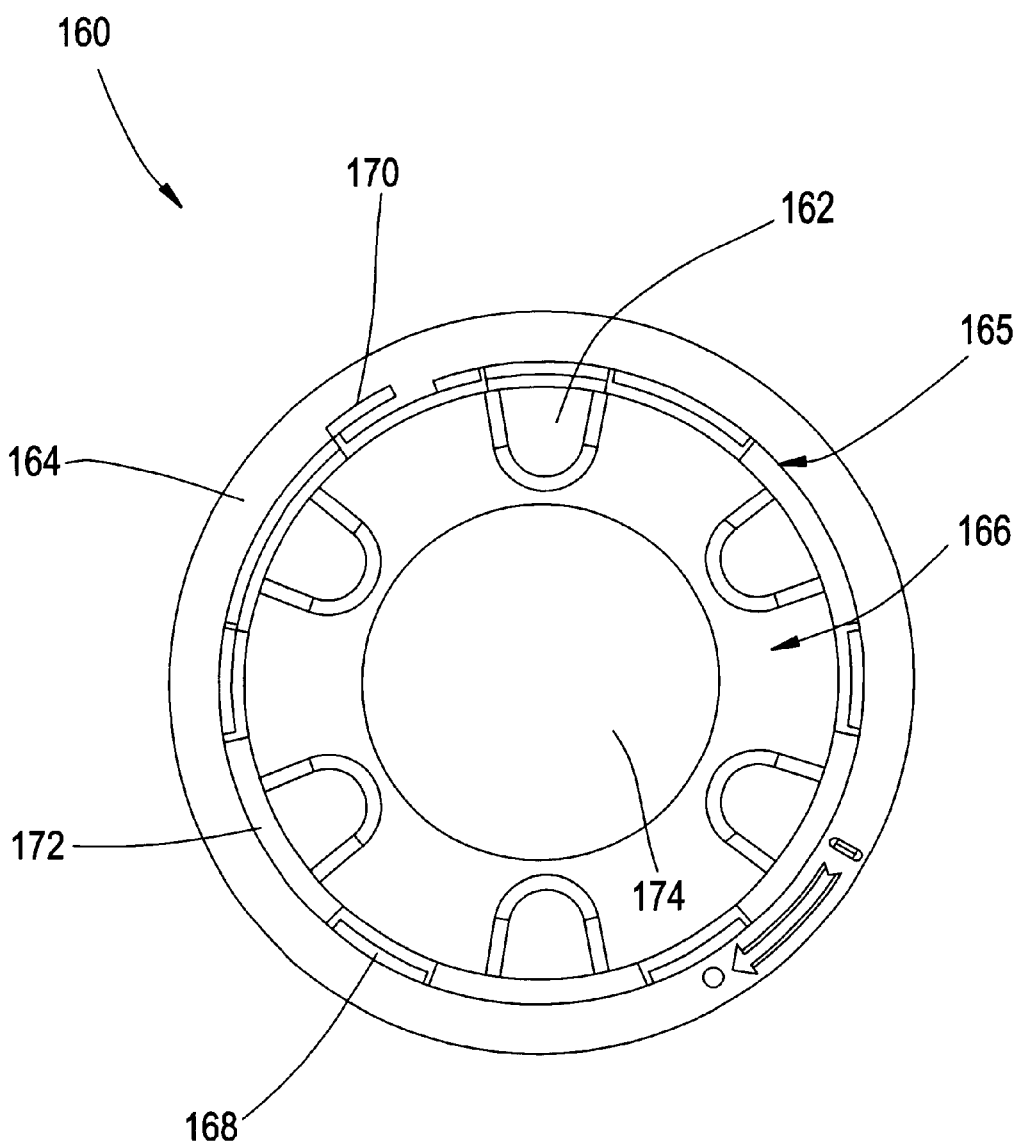
FIG. 19 is a top plan view of the channel plate of FIG. 18.

The dispensing assembly 114 of FIG. 5 includes a channel plate 160 as shown in FIGS. 18–19. The channel plate 160 is substantially a thin circular member with channels 162 formed therein. The channels 162 are sized and shaped accordingly to allow passage of a single earplug therethrough. The channels may further incorporate a universal design to allow passage therethrough of earplugs of varying sizes, shapes, and material compositions. The channel plate 160 further includes a rim 164 formed at a top surface 166. A slot 165 is formed in the top surface 166 adjacent an inside edge of the rim 164. Retaining flanges 168 and a locking feature 170 are formed integral to the rim 164 extending into the slot 165. The mounting flanges 168 are located on an inside of the rim 164 such that spaces 172 of the slot 165 are formed between adjacent mounting flanges 168 and between the mounting flanges 168 and the locking feature 170. A through hole 174 is formed in the center of the channel plate 160. The through hole 170 is substantially annular and is concentric with the annular shape of the channel plate 160. A mating flange 176 is integrally formed at a bottom surface 167 of the channel plate 160 opposite the top surface 166. The mating flange 176 facilitates adjoining the channel plate 160 and the remainder of the dispensing assembly 114.

Figure 20:
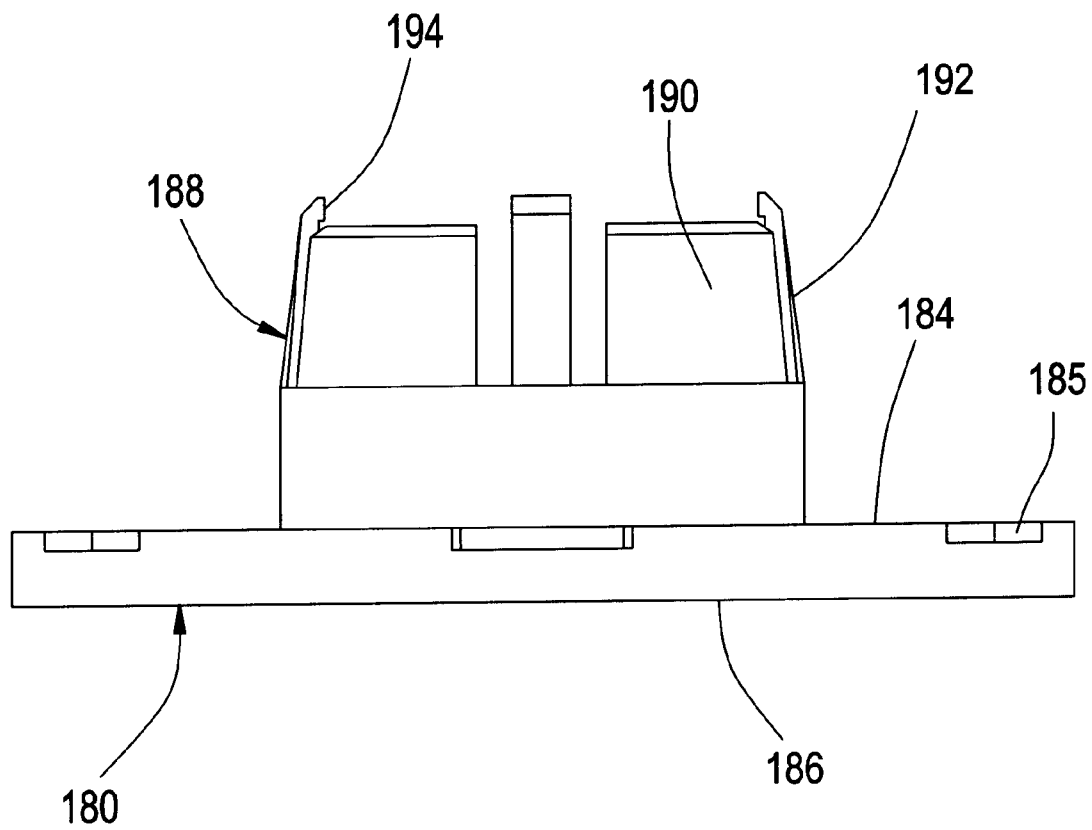
FIG. 20 is a side elevational view of a shutter plate in one embodiment according to the present invention.
Figure 21:
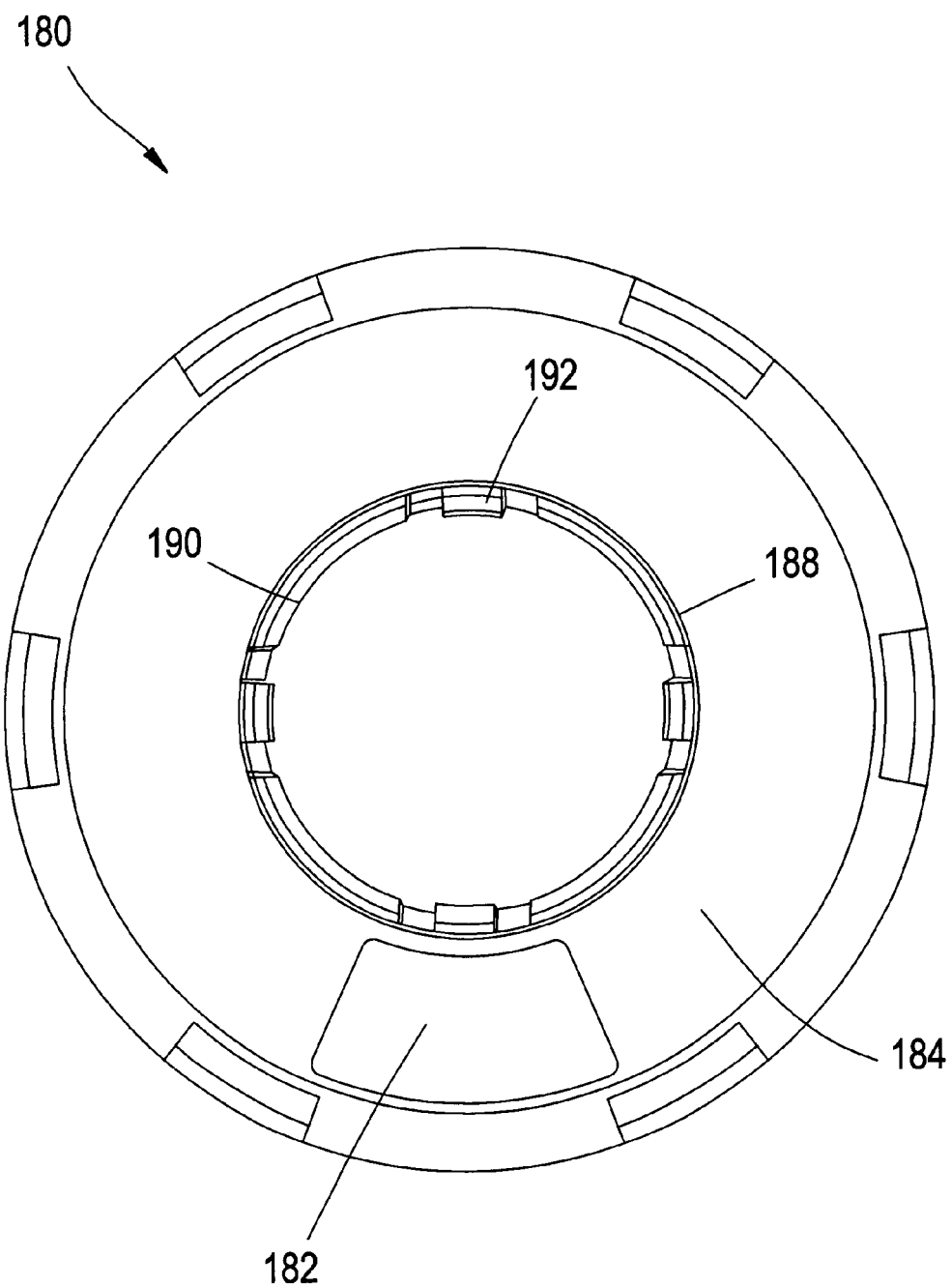
FIG. 21 is a top plan view of the shutter plate of FIG. 20.

The mounting assembly 114 of FIG. 5 further includes a shutter plate 180 as shown in FIGS. 20–21. The shutter plate 180 is an annular shaped member with a shutter opening 182 formed therein. The shutter opening 182 is sized and shaped appropriately to allow the passage therethrough of an earplug according to the present invention. The shutter plate 180 is defined by a top surface 184 and a bottom surface 186 formed opposite one another. The shutter plate 180 also features a hollow underside (not shown) proximate the bottom surface 186. Latch openings 185 are formed in the top surface 184 of the shutter plate 180. An impeller mount 188 is located on the top surface 184 of the shutter plate 180. The impeller mount 188 generally extends perpendicularly from the shutter plate 180. The impeller mount 188 is annular in cross-section and is fixably mounted to the top surface 184 in a concentric manner with the annular shape of the shutter plate 180. The impeller mount 188 includes mounting arms 190 and latching arms 192. The latching arms 192 include catches 194.

Figure 22:
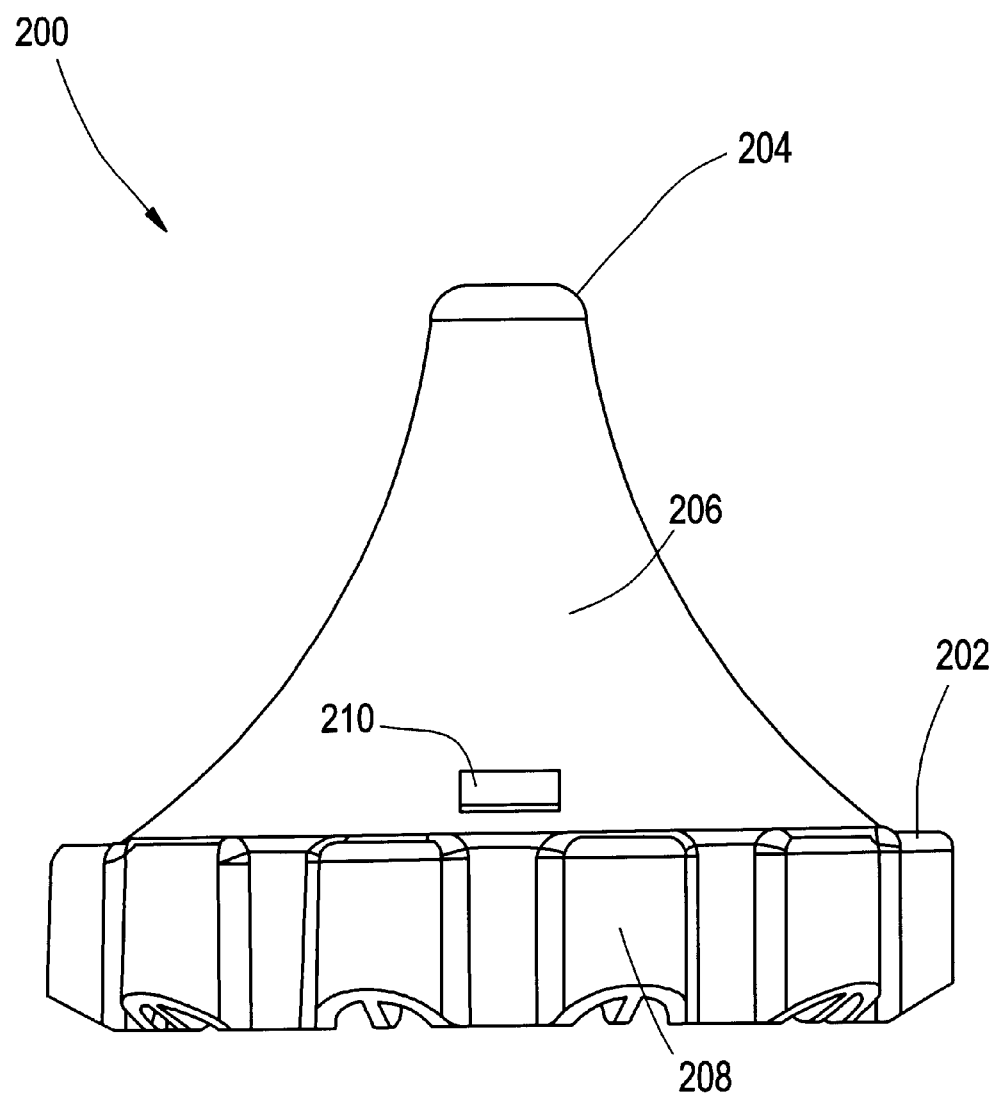
FIG. 22 is a side elevational view of an impeller in one embodiment according to the present invention.
Figure 23:
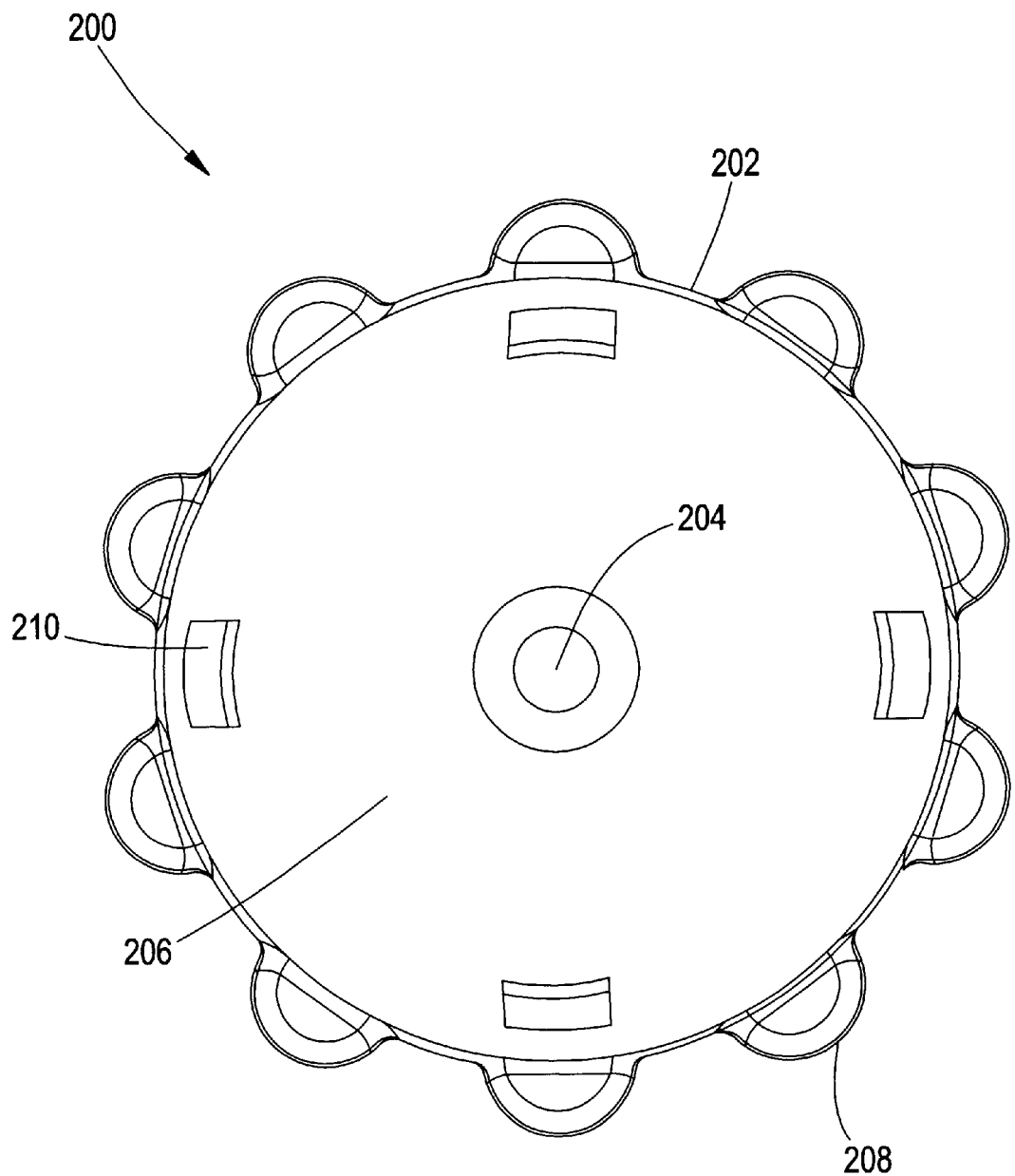
FIG. 23 is a top plan view of the impeller of FIG. 22.

The dispensing assembly 114 further includes an impeller 200 as shown in FIGS. 22–23. The impeller 200 is substantially frustoconical in shape with a hollow interior (not shown), the impeller 200 further including a base 202 and an apex 204 formed opposite one another. A body 206 of the impeller 200 is located between the base 202 and the apex 204. The base includes guiding protuberances 208 extending from the base 202, the protuberances 208 being any of a variety of shapes sufficient for directing the earplugs between adjacent protuberances 208 as discussed herein. The guiding protuberances 208 may, for example, be substantially rounded in shape. The body 206 of the impeller 200 includes mounting slots 210 formed therein. The mounting slots 210 may, in one embodiment, include four slots spaced equally about a circumference of the base 202. The body 206 may be further contoured to promote movement of the earplugs toward the guiding protuberances 208, as taught herein.

Figure 24:
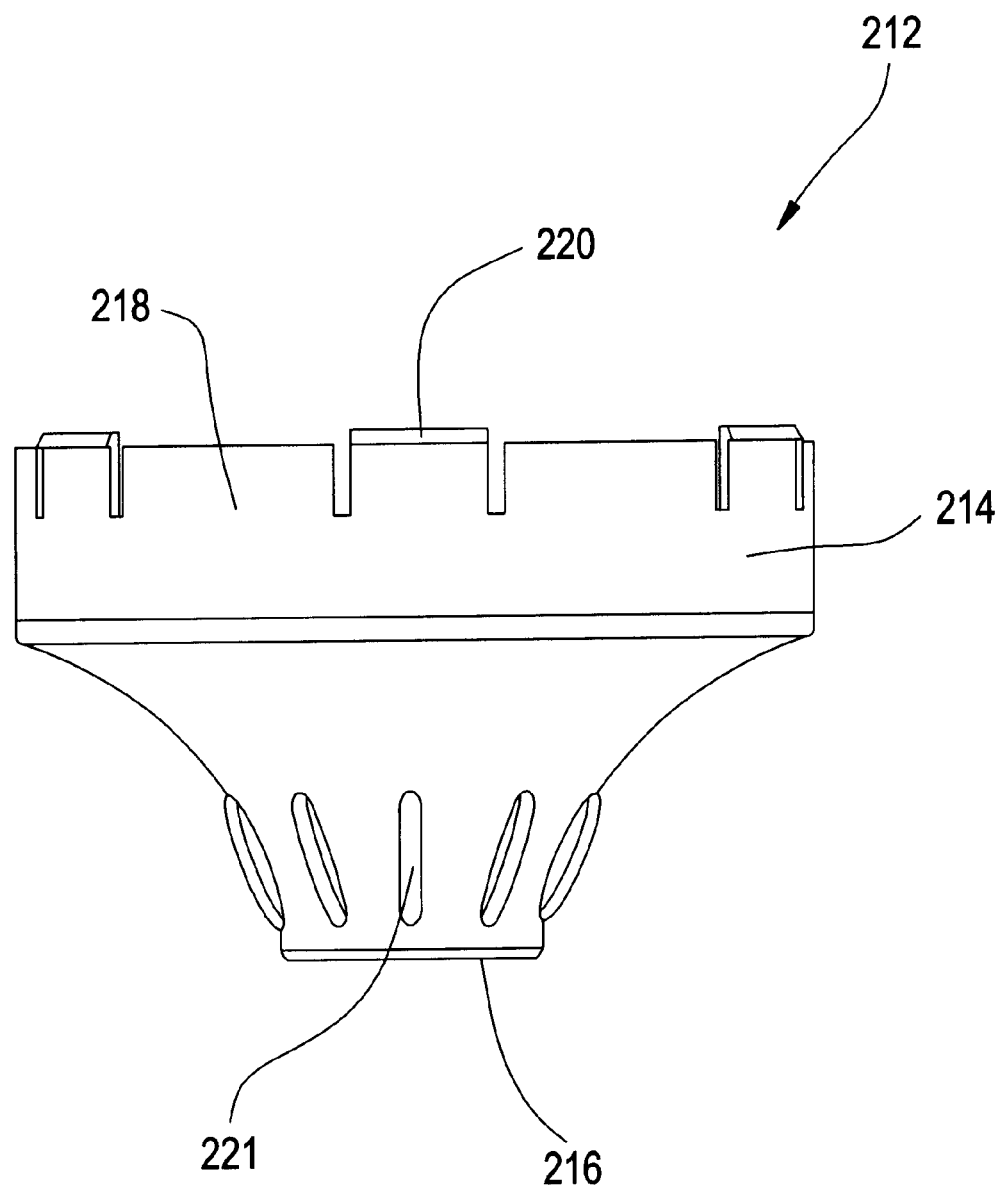
FIG. 24 is a side elevational view of a funnel in one embodiment according to the present invention.
Figure 25:
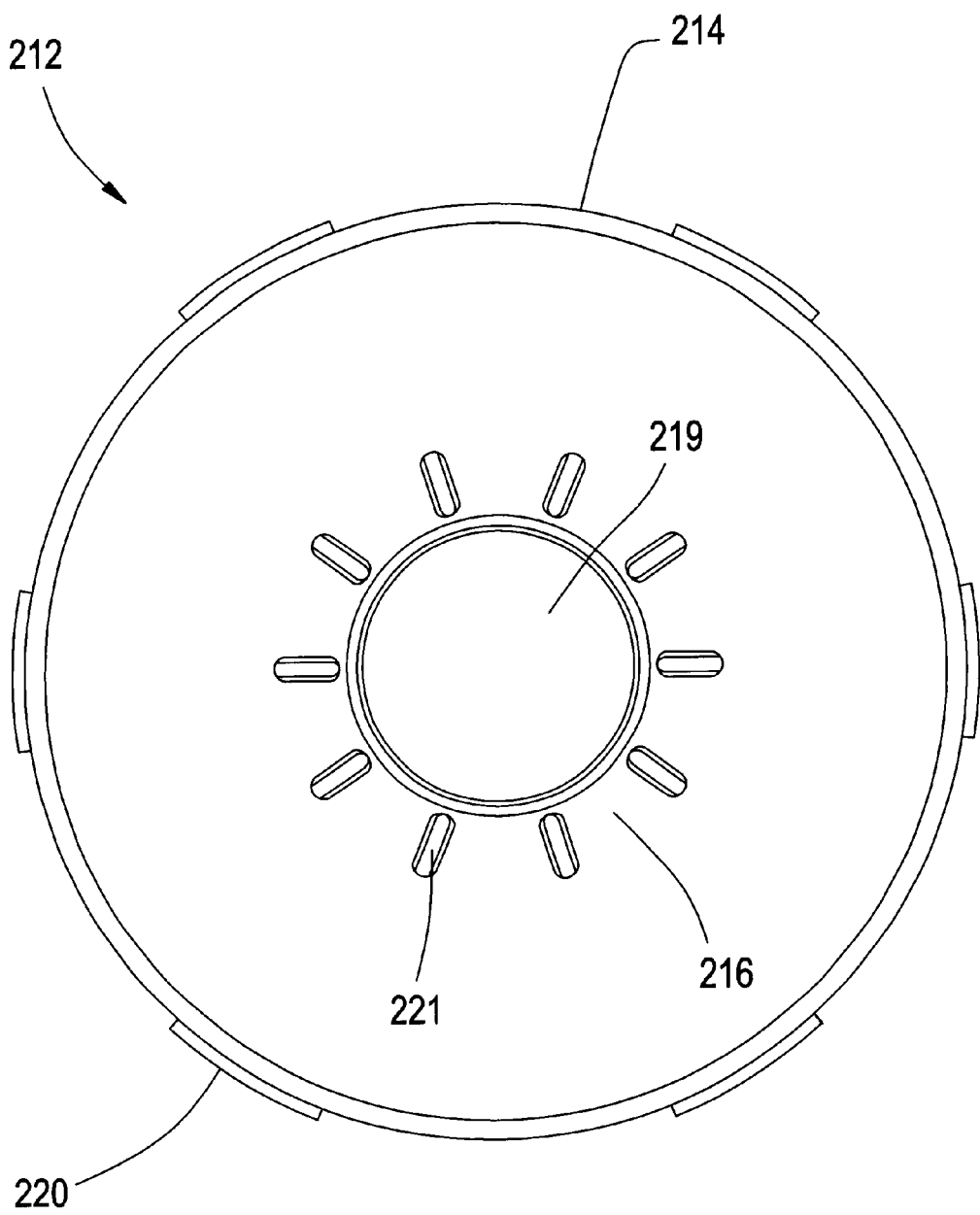
FIG. 25 is a bottom plan view of the funnel of FIG. 24.

Finally, referring to FIGS. 24–25, the dispensing assembly 114 of FIG. 5 includes a funnel member 212 having a mating end section 214 and a dispensing end 216. The mating end section 214 is cylindrical in shape and includes mating flanges 218 and latching flanges 220. The dispensing end 216 is substantially frustoconically shaped and includes a dispensing opening 219 formed therein. The dispensing end 216 of the funnel member 212 also includes gripping protuberances 221 located radially about the opening 218 for providing a hand grip for a user of the earplug dispenser 100 according to the present invention.

The assemblage of the dispensing assembly 114 of FIG. 5 is now discussed with reference to FIGS. 18–25. The top surface 184 of the shutter plate 180 is drawn toward the mating flange 176 of the channel plate 160. The impeller mount 188 located on the top surface 184 of the shutter plate 180 is inserted and passes through the through hole 174 of the shutter plate 180 such that the top surface 184 of the shutter plate 180 is adjacent the bottom surface 167 of the channel plate 160, the impeller mount 188 extending perpendicularly from the top surface 166 of the channel plate 160. The impeller mount 188 has a diameter slightly less than that of the through hole 174 while the shutter plate 180 has a diameter larger than that of the through hole 174. In this way, the impeller mount 188 may pass through the through hole 174 and the shutter plate 180 is retained adjacent the bottom surface 167 of the channel plate 160.

The impeller 200 is then attached to the impeller mount 188, locking the channel plate 160 therebetween. The impeller mount 188 is inserted in the hollow interior of the impeller 200. The mounting slots 210 receive the latching arms 192, the catches 194 affixing thereto, thus securing the impeller 200 to the impeller mount 188. The attachment of the impeller 200 and the impeller mount 188 about the channel plate 160 allows the impeller 200 and the shutter plate 180 to rotate, clockwise or counter clockwise, as a single unit relative to the channel plate 160.

Next, to complete the assemblage of the dispensing assembly 114, the funnel member 212 is attached to the shutter plate 180. The mating end 214 of the funnel member 212 is brought proximate the bottom surface 186 of the shutter plate 180. The mating flanges 218 and the latching flanges 220 are inserted into the hollow underside of the shutter plate 180. The latching flanges 220 are received in the latch openings 185 to secure the funnel member 212 to the shutter plate 180. In this way, the funnel member 212, the shutter plate 180, and the impeller 200 float about the channel plate 160 and, thus, may rotate as a single unit Ad relative to the channel plate 160.

The earplug dispenser 100 is assembled, in one embodiment of the present invention, by attaching the earplug container 116 to the dispensing assembly 114 and locating the attached assembly 114 and container 116 within the mounting assembly 112. The mounting of the earplug container 116 with the dispensing assembly 114 is described as follows with reference to FIGS. 17–19. The mouth portion 158 of the earplug container 116 is brought proximate the top surface 166 of the channel plate 160. The mouth portion 158 is inserted in the slot 165 such that the mounting flanges 159 pass through the spaces 172, locating the mounting flanges 159 below the mounting flanges 168. Then, the earplug container 116 is rotated about its vertical axis bringing the mounting flanges 159 adjacent the mounting flanges 168 such that the mounting flanges 159 are located between the mounting flanges 168 and the bottom surface 167 of the channel plate 160. In this way, the mounting flanges 159,168 contact one another resulting in a frictional retaining force therebetween. The described rotation of the container 116 further allows the mounting flange 159 to engage the locking feature 170 of the channel plate 160 thus securing the earplug container 116 to the dispensing assembly 114.

To complete the assemblage of the earplug dispenser 100, the dispensing assembly 114 as attached to the earplug container 116 is generally located within the mounting assembly 112 as now discussed with reference to FIGS. 3–20. The dispensing assembly 114 is brought proximate the upper portion 122 of the mounting assembly 112 such that the assembly 114 is located on the opposite side of the upper portion 122 from the base 118. The container 116 remains positioned distal the upper portion 122. The dispensing assembly 114 is lowered into the opening 152 formed by the ring mount 150 of the upper portion 122. The funnel 114 and the shutter plate 180 are of a diameter less than that of the opening 152, thus the funnel 114 and the shutter plate 180 pass through the opening 152. The rim 164 formed on the channel plate 160 is drawn near the mounting lip 154 of the ring mount 150. The assembly mounts 155 of the mounting lip 154 receive the assembly mounting flanges 168 of the channel plate 160. The rim 164 of the channel plate 160 is of a diameter substantially equivalent to that of the mounting lip 154, thus the rim 164 seats flush upon the mounting lip 154. The mounting lip 154 supports the downward load of the dispensing assembly 114 and the attached earplug container 116. The assembly mounts 155 prevent rotational movement of the channel plate 160 and the earplug container 116 attached thereto. The earplug dispenser 100 may then be placed, free-standing atop the base 118, in an appropriate location, for instance, on a table top in a work space. Alternatively, the mounting assembly 112 may be initially affixed to a structure, such as a wall, as described above. Then, the dispensing assembly 114 and the attached earplug container 116 may be secured within the mounting assembly 112 as taught.

The entire earplug dispenser 100, taught herein, may be constructed of disposable materials such as, for example, plastics. Further, the dispenser 100 may be composed of recyclable materials. In this way, when the earplug container 116 due to usage becomes empty of earplugs, the earplug dispenser 100 may be safely disposed or recycled as appropriate. Alternatively, when the container 116 becomes devoid of earplugs, only the dispensing assembly 114 and the attached earplug container 116 may be discarded while the mounting assembly 112 is re-used. Further still, both the mounting assembly 112 and the dispensing assembly 114 as attached to the earplug container 116 may be re-used by simply removing the container 116 from the assembly 114 and refilling the container 116 with a new stock of earplugs.

It will be understood that although the earplug assembly 100 was described herein as including a plurality of inter-attaching parts, the mounting assembly 112, the dispensing assembly 114, and the earplug container 116 may each be single integrally formed molded pieces which are attached to one another to form the dispenser 100. Further, the dispensing assembly 114 and the earplug container 116 may be integrally formed such that disassembly thereof would not be an option, thus making the integral assembly 114/container 116 a disposable unit to be discarded upon depletion of the earplugs stored therein.

The use of the earplug dispenser of the present invention will now be discussed with reference to FIGS. 3–25. The earplug dispenser provides a convenient, efficient means for distributing a pair of earplugs while preventing excessive handling and soiling of the earplugs and concurrently reducing resulting waste products. A plurality of earplugs are placed in the earplug container 116 and the earplug dispenser 100 is assembled as discussed above. An operator of the dispenser 100 clasps by hand the dispensing end 216 of the funnel member 212, the dispensing end 216 being located between the upper portion 122 and the base 118 of the mounting assembly 112. The operator then rotates the funnel member 212 and thereby correspondingly rotates the shutter plate 180 and the impeller 200 which are fixably attached to the funnel 212. The gripping protuberances 221 may be used by the operator to facilitate hand grip on the funnel member 212. The funnel member 212 may be rotated clockwise or counter-clockwise. As mentioned, manual rotation of the funnel correspondingly rotates the shutter plate 180 and the impeller 200. Such rotation, as discussed herein above, is relative to the channel plate 160 which is held fixed in a non-rotatable position by the interaction of the assembly mounting flanges 168 of the channel plate 160 and the assembly mounts 155 formed in the upper portion 122 of the mounting assembly 112. Rotation of the impeller 200 within the earplug container 116 stirs the individual earplugs stored in the hopper portion 156 of the container 116, thus encouraging the descent of the earplugs from the hopper portion 156 toward the mouth portion 158 of the earplug container 116. Due to the relative shapes of the earplug container 116 and the impeller 200 in conjunction with the stirring action of the rotating impeller 200, the earplugs settle on the top surface 166 of the channel plate 160 and enter the channels 162 formed therein. Beneath the channel plate 160, the shutter plate 180 rotates concurrently with the impeller 200 and the funnel 212. This rotation of the shutter plate 180 displaces the shutter opening 182 in a circumferential path proximate the bottom surface 167 of the channel plate 160. As the shutter opening 182 aligns with a particular channel 162, a passageway is created from the interior of the earplug container 116, through the channel plate 160, and through the shutter plate 180 into the funnel member 212. Thus, an earplug located in the channel 162 as described, will pass through the channel plate 160, the shutter plate 180, and will drop into the funnel member 212 due to gravity when the shutter opening 182 is rotated into alignment with the particular channel 162. Upon deposition into the funnel member 212, gravity will draw the earplug toward the dispensing end 216 due to the conical shape of the body 206 of the funnel member 212. Finally, the earplug passes through the dispensing opening 219 of the funnel member 212 and is deposited into the hand of the operator. Additional rotation of the funnel will similarly deposit a second earplug into the waiting hand of the operator.

The earplug dispenser 100 of the present invention has been described thus far as being manually operable. However, it will be understood that the dispenser 100 may be operated by an alternate means such as, for example, electronically or pneumatically. In one alternate embodiment, the earplug dispenser 100 may include a sensor which detects the operator's hand beneath the funnel member 212 and thus, accordingly, a controller rotates the funnel thus bringing the shutter opening 182 into alignment with the channel 162 and allowing dispensation of an earplug.

The present invention, as taught herein, allows for the dispensing of a controlled number of earplugs thus reducing the waste and inefficiency associated with dispensing is excess earplugs in amounts greater than what is needed by a particular operator. Further, the present invention stores unwrapped individual earplugs for distribution thus eliminating incidental packaging waste associated with commonly used packaged earplugs. Additionally, overall handling of the individual earplugs is greatly reduced thus preserving the integrity of the earplugs prior to dispensation.

The impeller of the present invention does not drag the earplugs about the bottom of the earplug container in attempts to push the earplugs to a dispensing opening as is seen in the prior art described herein above. Instead, the impeller of the present invention simply stirs the earplugs within the container causing the earplugs to settle toward the channel plate where the earplugs ultimately enter the channels as described herein above. In this way, the present invention negates the frictional forces associated with dragging the earplugs about the bottom of the container thereby avoiding the jamming of earplugs between the impeller blades and the container base common in the prior art, thus resulting in a more efficient and a more easily operable earplug dispenser.

Additionally, due to the novel design of the channels formed within the channel plate, the dispensing assembly of the present invention may accommodate and allow passage therethrough of earplugs of a variety of shapes, sizes, and material compositions. Further, it will be noted that the interior surfaces of the earplug dispenser described herein, that is, those surfaces of the dispenser which directly contact the earplugs, may be contoured, textured, or Rio kept smooth to further inhibit dispensation of the earplugs from the container through the dispensing assembly and ultimately to the operator with a high degree of efficiency and exactitude.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An earplug dispenser comprising:
    a container for storing earplugs at an interior of the container, the container having at least one container opening formed therein through which the earplugs are dispensed to an the container;
    a shutter assembly located at the exterior of the container proximate the container opening, the shutter assembly having at least one shutter opening formed therein; and
    a funnel member coupled to the shutter assembly for guiding dispensed earplugs;
    wherein the shutter assembly is rotationally movable for bringing the shutter opening into alignment with the container opening to allow the earplugs to pass from the interior of the container, through the shutter assembly, and through the funnel member to the exterior.

2. The earplug dispenser of claim 1, wherein the shutter assembly comprises an annular plate with the at least one shutter opening formed therein, the annular plate being manually rotatable relative to the container opening allowing rotational movement of the shutter opening.

3. The earplug dispenser of claim 1, further comprising a mounting assembly upon which the container, the shutter assembly, and the dispensing flange are mounted.

4. The earplug dispenser of claim 3, wherein the mounting assembly comprises a base, a neck fixed to the base and an upper portion attached to the neck opposite the base for receiving and retaining the container, the shutter assembly, and the funnel member.

5. The earplug dispenser of claim 1, further comprising a channel member coupled to the container opening and located between the shutter assembly and the container, the channel member comprising channels formed therein for allowing passage of the earplugs.

6. The earplug dispenser of claim 5, wherein the channels are formed to allow passage of earplugs of a variety of shapes, sizes, and compositions.

7. The earplug dispenser of claim 5, wherein the channel member further comprises a through opening formed therein.

8. The earplug dispenser of claim 1, further comprising an impeller located at an inside of the container, the impeller being rotatably attached to the shutter assembly such that rotation of the shutter assembly rotates the impeller.

9. The earplug dispenser of claim 8 wherein the impeller is contoured to stir the earplugs within the container and to facilitate movement of the earplugs toward the container opening.

10. The earplug dispenser of claim 1, wherein the funnel member is disposed such that rotation of the funnel member rotates the shutter assembly.

11. The earplug dispenser of claim 1, wherein the funnel member comprises a hand grip.

12. An earplug dispenser comprising:
   a container for storing earplugs, the container having at least one container opening formed therein through which the earplugs are dispensed;
   a shutter assembly located at the container opening, the shutter assembly having at least one shutter opening formed therein; and
   a funnel member coupled to the shutter assembly for guiding dispensed earplugs;
   a channel member coupled to the container opening and located between the shutter assembly and the container, the channel member comprising channels formed therein for allowing passage of the earplugs; and
   an impeller located on the channel member at an inside of the container, the impeller being rotatably attached to the shutter assembly through a through opening formed in the channel member such that rotation of the shutter assembly correspondingly rotates the impeller;
   wherein the shutter assembly is selectively movable to bring the shutter opening into alignment with the container opening to allow the earplugs to pass from the container, through the shutter assembly, and through the funnel member.

13. An earplug dispenser comprising:
   a container for containing earplugs, the container having at least one container opening formed therein; and
   a dispensing mechanism coupled to the container, the dispensing mechanism having at least one dispensing opening formed therein;
   wherein the dispensing mechanism is rotatable relative to the container so that the at least one dispensing opening may be rotationally positioned in alignment with the at least one container opening to allow passage of said earplugs from the container through the container opening and through the dispensing opening to an outside of the container.

14. The earplug dispenser of claim 13, wherein the dispensing mechanism comprises an annular shutter plate in which the dispensing opening is formed, the annular shutter plate being rotatable relative to the container and relative to the container opening such that the dispensing opening may be rotationally brought into alignment with the container opening to allow passage of the earplugs.

15. The earplug dispenser of claim 13, wherein the dispensing mechanism comprises:
   a funnel member for dispensing the earplugs, the funnel member attached to a side of the dispensing mechanism and rotatable therewith; and
   an impeller attached to an opposite side of the dispensing mechanism and rotatable therewith;
   wherein the impeller extends into an interior of the container adjacent the container opening such that by rotating the funnel member, the dispensing mechanism and the impeller are correspondingly rotated and the impeller guides the earplugs to the container opening.

16. The earplug dispenser of claim 15, wherein the container comprises an annular channel plate in which the container opening is formed, the channel plate being fixed to the container at the container opening.

17. The earplug dispenser of claim 16, wherein the dispensing mechanism further comprises an annular shutter plate having the dispensing opening formed therein, the shutter plate being fixed at a first side to the funnel member and being rotatably coupled to the channel plate at a second side such that, by rotating the funnel member, the dispensing opening is rotationally movable into alignment with the container opening.

18. A method of dispensing earplugs from an earplug dispenser, the dispenser including an earplug container for containing the earplugs having a first opening formed therein, a shutter assembly disposed at an exterior of the container having a second opening formed therein, and an impeller coupled with the shutter assembly and extending into an interior of the container, the method comprising:
   rotating the shutter assembly outside of the earplug container;
   stirring the earplugs and guiding the earplugs with the impeller to the first opening;
   rotationally aligning the second opening with first opening; and
   passing the earplugs through the aligned first and second openings to the exterior of the earplug container.

* * * * *

UNITED STATES PATENT AND TRADEMARK OFFICE
CERTIFICATE OF CORRECTION

PATENT NO. : 6,604,653 B2  
APPLICATION NO. : 09/891808  
DATED : August 12, 2003  
INVENTOR(S) : Timothy A. Millar Page 1 of 1

It is certified that error appears in the above-identified patent and that said Letters Patent is hereby corrected as shown below:

<u>Column 3:</u>  
Line 50, before "Referring" delete "To"

<u>Column 4:</u>  
Line 19, before "FIG 18" delete "Iris"

<u>Column 7:</u>  
Line 58, before "relative" delete "Ad"

<u>Column 10:</u>  
Line 37, after "or" delete "Rio"  
Line 52, after "an" insert --exterior of--

Signed and Sealed this

Eighth Day of May, 2007

JON W. DUDAS  
*Director of the United States Patent and Trademark Office*